United States Patent
Nguyen et al.

(10) Patent No.: US 11,666,239 B2
(45) Date of Patent: Jun. 6, 2023

(54) BIODEGRADABLE PRESSURE SENSOR

(71) Applicant: University of Connecticut, Farmington, CT (US)

(72) Inventors: Thanh Duc Nguyen, Vernon, CT (US); Eli Curry, North Franklin, CT (US)

(73) Assignee: UNIVERSITY OF CONNECTICUT, Farmington, CT (US)

(*) Notice: Subject to any disclaimer, the term of this patent is extended or adjusted under 35 U.S.C. 154(b) by 681 days.

(21) Appl. No.: 16/491,614

(22) PCT Filed: Mar. 14, 2018

(86) PCT No.: PCT/US2018/022441
§ 371 (c)(1),
(2) Date: Sep. 6, 2019

(87) PCT Pub. No.: WO2018/170132
PCT Pub. Date: Sep. 20, 2018

(65) Prior Publication Data
US 2021/0127998 A1 May 6, 2021

Related U.S. Application Data

(60) Provisional application No. 62/471,146, filed on Mar. 14, 2017, provisional application No. 62/470,968, filed on Mar. 14, 2017.

(51) Int. Cl.
*A61B 5/03* (2006.01)
*A61B 5/00* (2006.01)

(52) U.S. Cl.
CPC .............. *A61B 5/03* (2013.01); *A61B 5/6867* (2013.01); *A61B 2562/0209* (2013.01);
(Continued)

(58) Field of Classification Search
CPC .......... A61B 5/03; A61B 5/031; A61B 5/032; A61B 5/033; A61B 5/036; A61B 5/6867;
(Continued)

(56) References Cited

U.S. PATENT DOCUMENTS 589,119 A 8/1897 Burgess
4,438,773 A 3/1984 Letterio
(Continued)

FOREIGN PATENT DOCUMENTS

CN 102657914 B 5/2015
CN 106109792 A 11/2016
(Continued)

OTHER PUBLICATIONS

Boutry, et al., "A sensitive and Biodegradable Pressure Sensor Array for Cardiovascular Monitoring," Adv. Mater., Nov. 18, 2015:27(43):6954-6961.
(Continued)

*Primary Examiner* — Devin B Henson
(74) *Attorney, Agent, or Firm* — Michael Best & Friedrich LLP

(57) ABSTRACT

A biodegradable pressure sensor for measuring vital physiological pressures and for preventing the buildup of dangerous internal forces in impaired organs. The pressure sensor is constructed by depositing Mg or Mo on both sides of a PLLA film. This layered configuration (Mg/PLLA/Mg) or (Mo/PLLA/Mo) may then be encapsulated by layers of high molecular weight PLA. These materials are biodegradable such that after implantation, the sensor does not require invasive removal surgery that can damage directly interfaced tissues.

22 Claims, 13 Drawing Sheets

(52) U.S. Cl.
CPC ............... *A61B 2562/0247* (2013.01); *A61B 2562/0261* (2013.01); *A61B 2562/16* (2013.01)

(58) Field of Classification Search
CPC .............. A61B 3/16; A61B 2562/0209; A61B 2562/0247; A61B 2562/0261; A61B 2562/16; A61B 2562/18
See application file for complete search history.

(56) References Cited

U.S. PATENT DOCUMENTS

| | | | |
|---|---|---|---|
| 5,131,276 | A | 7/1992 | Kibblewhite |
| 5,246,013 | A | 9/1993 | Frank et al. |
| 5,287,331 | A | 2/1994 | Schindel et al. |
| 5,306,620 | A | 4/1994 | Ginsberg et al. |
| 5,443,495 | A | 8/1995 | Buscemi et al. |
| 5,498,499 | A | 3/1996 | Flow et al. |
| 5,512,600 | A | 4/1996 | Mikos et al. |
| 5,514,378 | A | 5/1996 | Mikos et al. |
| 5,678,565 | A | 10/1997 | Sarvazyan |
| 5,697,901 | A | 12/1997 | Eriksson |
| 5,794,023 | A | 8/1998 | Hobbs et al. |
| 5,827,198 | A | 10/1998 | Kassal |
| 6,142,948 | A | 11/2000 | Toda |
| 6,219,574 | B1 | 4/2001 | Cormier et al. |
| 6,334,856 | B1 | 1/2002 | Allen et al. |
| 6,447,887 | B1 | 9/2002 | Claus et al. |
| 6,468,219 | B1 | 10/2002 | Njemanze |
| 6,627,421 | B1 | 9/2003 | Unger et al. |
| 6,835,377 | B2 | 12/2004 | Goldberg et al. |
| 7,001,372 | B2 | 2/2006 | Richter |
| 7,184,826 | B2 | 2/2007 | Cormier et al. |
| 7,332,197 | B2 | 2/2008 | Wood et al. |
| 7,344,499 | B1 | 3/2008 | Prausnitz et al. |
| 7,396,537 | B1 | 7/2008 | Krupnick et al. |
| 7,879,093 | B2 | 2/2011 | Wei et al. |
| 7,906,223 | B2 | 3/2011 | Rakow et al. |
| 8,067,110 | B2 | 11/2011 | Rakow et al. |
| 8,162,901 | B2 | 4/2012 | Gonnelli et al. |
| D659,820 | S | 5/2012 | Abel et al. |
| 8,301,262 | B2 | 10/2012 | Mi et al. |
| 8,469,936 | B2 | 6/2013 | Robinson et al. |
| 8,708,966 | B2 | 4/2014 | Allen et al. |
| 8,798,932 | B2 | 8/2014 | Boyden et al. |
| 8,946,974 | B2 | 2/2015 | Yu et al. |
| 8,955,515 | B2 | 2/2015 | Rakow et al. |
| 9,040,087 | B2 | 5/2015 | Boyden et al. |
| 9,050,053 | B2 | 6/2015 | Morgan |
| 9,089,677 | B2 | 7/2015 | Soo et al. |
| 9,192,655 | B2 | 11/2015 | Arinzeh et al. |
| 9,381,680 | B2 | 7/2016 | Oh et al. |
| 9,444,030 | B2 | 9/2016 | Wang et al. |
| 9,527,257 | B2 | 12/2016 | Lipton et al. |
| 9,795,774 | B2 | 10/2017 | Takada et al. |
| 9,846,091 | B2 | 12/2017 | Lu et al. |
| 9,849,270 | B2 | 12/2017 | Stockholm |
| 10,004,790 | B2 | 6/2018 | D'Souza |
| 10,098,574 | B1 | 10/2018 | Kam |
| 10,245,421 | B2 | 4/2019 | Ross |
| 10,292,831 | B2 | 5/2019 | Zellmer et al. |
| 10,500,300 | B2 | 12/2019 | Dybe et al. |
| 10,617,880 | B2 | 4/2020 | Zellmer et al. |
| 10,632,653 | B2 | 4/2020 | Niitsu et al. |
| 10,710,011 | B2 | 7/2020 | Inoue et al. |
| 2002/0081732 | A1 | 6/2002 | Bowlin et al. |
| 2002/0082543 | A1 | 6/2002 | Park et al. |
| 2004/0015211 | A1 | 1/2004 | Nurmikko et al. |
| 2004/0018226 | A1 | 1/2004 | Wnek et al. |
| 2004/0028655 | A1 | 2/2004 | Nelson et al. |
| 2005/0248547 | A1 | 11/2005 | Kent et al. |
| 2006/0043843 | A1 | 3/2006 | Sugiura et al. |
| 2006/0050189 | A1 | 3/2006 | Ito et al. |
| 2006/0107749 | A1 | 5/2006 | Liu et al. |
| 2006/0190080 | A1 | 8/2006 | Danoff et al. |
| 2006/0224237 | A1 | 10/2006 | Furst et al. |
| 2007/0141106 | A1 | 6/2007 | Bonutti et al. |
| 2007/0225631 | A1 | 9/2007 | Bowlin et al. |
| 2007/0255422 | A1 | 11/2007 | Wei et al. |
| 2007/0270738 | A1 | 11/2007 | Wu et al. |
| 2007/0293912 | A1 | 12/2007 | Cowan et al. |
| 2008/0009802 | A1 | 1/2008 | Lambino et al. |
| 2008/0058633 | A1 | 3/2008 | Boyden et al. |
| 2008/0269666 | A1 | 10/2008 | Wang et al. |
| 2009/0030365 | A1 | 1/2009 | Tokumoto et al. |
| 2009/0062723 | A1 | 3/2009 | Skiba |
| 2009/0163965 | A1 | 6/2009 | Boyden et al. |
| 2009/0182306 | A1 | 7/2009 | Lee et al. |
| 2009/0192431 | A1 | 7/2009 | Horstmann et al. |
| 2009/0280153 | A1 | 11/2009 | Hunter et al. |
| 2010/0152644 | A1 | 6/2010 | Pesach et al. |
| 2011/0028905 | A1 | 2/2011 | Takada |
| 2011/0109204 | A1 | 5/2011 | Tajitsu et al. |
| 2011/0230747 | A1 | 9/2011 | Rogers et al. |
| 2011/0242310 | A1 | 10/2011 | Beebe et al. |
| 2012/0197155 | A1 | 8/2012 | Mattes et al. |
| 2012/0226295 | A1 | 9/2012 | Jabbari |
| 2013/0005708 | A1 | 1/2013 | Lalwani |
| 2013/0041244 | A1* | 2/2013 | Woias ................... G01L 1/142 |
| | | | 600/381 |
| 2013/0086703 | A1 | 4/2013 | Maruyama et al. |
| 2013/0140649 | A1 | 6/2013 | Rogers et al. |
| 2014/0005606 | A1 | 1/2014 | Chen et al. |
| 2014/0145365 | A1 | 5/2014 | Omenetto et al. |
| 2015/0073551 | A1 | 3/2015 | Uehlin |
| 2015/0134061 | A1 | 5/2015 | Friis et al. |
| 2015/0165020 | A1 | 6/2015 | Jaklenec et al. |
| 2016/0005951 | A1 | 1/2016 | Yoshida et al. |
| 2016/0050750 | A1 | 2/2016 | Rogers et al. |
| 2016/0067375 | A1 | 3/2016 | Holmes et al. |
| 2016/0095599 | A1 | 4/2016 | Jose et al. |
| 2016/0175408 | A1 | 6/2016 | Chang et al. |
| 2016/0184571 | A1 | 6/2016 | Admati |
| 2016/0184595 | A1 | 6/2016 | Hossainy |
| 2016/0190427 | A1 | 6/2016 | Kim et al. |
| 2016/0287668 | A1 | 10/2016 | Tankovich |
| 2017/0020402 | A1 | 1/2017 | Rogers et al. |
| 2017/0027168 | A1 | 2/2017 | Heath |
| 2017/0080196 | A1 | 3/2017 | Lee et al. |
| 2017/0179370 | A1 | 6/2017 | Kim et al. |
| 2017/0189660 | A1 | 7/2017 | Baek |
| 2017/0252546 | A1 | 9/2017 | Park et al. |
| 2017/0258738 | A1 | 9/2017 | DeMuth et al. |
| 2017/0268942 | A1 | 9/2017 | Pedder et al. |
| 2017/0306295 | A1 | 10/2017 | Hazot et al. |
| 2017/0368321 | A1 | 12/2017 | Baek |
| 2018/0055643 | A1 | 3/2018 | Castro et al. |
| 2018/0140817 | A1 | 5/2018 | Spector |
| 2018/0289616 | A1 | 10/2018 | Chen et al. |
| 2018/0325806 | A1 | 11/2018 | Litvack et al. |
| 2019/0142318 | A1 | 5/2019 | Diebold et al. |
| 2019/0209819 | A1 | 7/2019 | Ross |
| 2019/0217071 | A1 | 7/2019 | Engel et al. |
| 2019/0269895 | A1 | 9/2019 | Nguyen et al. |
| 2019/0307697 | A1 | 10/2019 | Ma et al. |
| 2019/0319181 | A1 | 10/2019 | Melandso et al. |
| 2019/0328285 | A1 | 10/2019 | Liu |
| 2019/0330771 | A1 | 10/2019 | Takumi et al. |
| 2020/0009767 | A1 | 1/2020 | Li |
| 2020/0093966 | A1 | 3/2020 | Rabolt et al. |
| 2020/0276018 | A1 | 9/2020 | Nguyen et al. |
| 2020/0276365 | A1 | 9/2020 | Nguyen et al. |
| 2020/0282350 | A1 | 9/2020 | Inoue et al. |
| 2020/0292206 | A1 | 9/2020 | Tamakura et al. |
| 2020/0313066 | A1 | 10/2020 | Getman |
| 2021/0283387 | A1 | 9/2021 | Silbart et al. |
| 2021/0378949 | A1 | 12/2021 | Nguyen et al. |
| 2021/0379249 | A1 | 12/2021 | Nguyen et al. |
| 2022/0096371 | A1 | 3/2022 | Nguyen et al. |
| 2022/0176171 | A1 | 6/2022 | Nguyen et al. |

FOREIGN PATENT DOCUMENTS

| | | |
|---|---|---|
| EP | 0955359 B1 | 1/2009 |
| EP | 1993621 B1 | 8/2011 |

(56) References Cited

FOREIGN PATENT DOCUMENTS

| | | |
|---|---|---|
| EP | 1715915 B1 | 11/2012 |
| EP | 2482772 B1 | 10/2018 |
| EP | 3542740 A1 | 9/2019 |
| IN | 202041031484 A | 7/2020 |
| KR | 101832716 B1 | 2/2018 |
| RU | 2082467 C1 | 6/1997 |
| WO | 2006057987 A1 | 6/2006 |
| WO | WO2006057987 A1 | 6/2006 |
| WO | 2008085904 A1 | 7/2008 |
| WO | WO2008085904 A1 | 7/2008 |
| WO | 2012103257 A2 | 8/2012 |
| WO | WO 2012127224 A1 | 9/2012 |
| WO | WO 2013101908 A1 | 7/2013 |
| WO | WO 2014143412 A8 | 11/2014 |
| WO | 2017003238 A1 | 1/2017 |
| WO | WO2017011320 A1 | 1/2017 |
| WO | WO 2017139253 A1 | 8/2017 |
| WO | WO 2017151715 A1 | 9/2017 |
| WO | WO 2018017196 A1 | 1/2018 |
| WO | WO 2018089918 A1 | 5/2018 |
| WO | WO 2018114871 A1 | 6/2018 |
| WO | WO 2018170132 A1 | 9/2018 |
| WO | WO 2019025625 A1 | 2/2019 |
| WO | WO 2019094349 A1 | 5/2019 |
| WO | 2019143293 A1 | 7/2019 |

OTHER PUBLICATIONS

International Search Report, PCT/US2018/022441, dated Aug. 1, 2018.
Written Opinion, PCT/US2018/022441, dated Aug. 1, 2018.
Amini et al., "Bone tissue engineering: recent advances and challenges," Critical Reviews™ in Biomedical Engineering, 2012, 40,(5):363-408.
Anglen, "The clinical use of bone stimulators," Journal of the Southern Orthopaedic Association, 2002, 12, (2), 46-54.
Bauer et al., "Bone Graft Materials: An Overview of the Basic Science," Clinical orthopaedics and related research, 2000, 371, 10-27.
Bussemer et al., "Pulsatile drug-delivery systems," Crit Rev Ther Drug Syst., 2001, 18(5):433-458, Abstract.
Carpentier et al., "Clinical trial of blood-brain barrier disruption by pulsed ultrasound," Science translational medicine, 2016, 8(343):343re2, 9 pages.
Chen et al., "Fully embeddable chitosan microneedles as a sustained release depot for intradermal vaccination," Biomaterials, 2013, 34(12):3077-3086.
Chiappini et al., "Biodegradable silicon nanoneedles delivering nucleic acids intracellularly induce localized in vivo neovascularization," Nature Materials, 2015, 14:532-539.
Cohen et al., "Totally implanted direct current stimulator as treatment for a nonunion in the foot," The Journal of foot and ankle surgery: official publication of the American College of Foot and Ankle Surgeons, 1993, 32, (4), 375-381.
Csafeglobal, The Cost of a Broken Vaccine Cold Chain Part Two, Financial Cost. <http://csafeglobal.com/the-cost-of-a-broken-vaccine-cold-chain-part-two-financial-cost-1> Sep. 17, 2014, 3 pages.
Curry et al., "Biodegradable piezoelectric force sensor," PNAS, 2018, 115(5):909-914.
Dai et al., "Electrospun emodin polyvinylpyrrolidone blended nanofibrous membrane: a novel medicated biomaterial for drug delivery and accelerated wound healing," Journal of Materials Science: Materials in Medicine, 2012, 23(11):2709-2716.
Demiray, "Electro-mechanical remodelling of bones," International Journal of Engineering Science, 1983, 21, (9), 1117-1126.
Ferreira et al., "Bone Collagen Role in Piezoelectric Mediated Remineralization," Acta Microscopica, 2009, 18(3):278-286.
Glazner et al., "Cost of vaccine administration among pediatric practices," Pediatrics, 2009, 124(Supplement 5):S492-S498.

Graf et al., "In Stimulation of bone growth by implanted FEP electrets and PVDF piezoelectric films," Proceedings 5th International Symposium on Electrets (ISE 5), Heidelberg, 1985, pp. 813-818.
Habibovic, "Strategic directions in osteoinduction and biomimetics," Tissue Engineering Part A, 2017, 23, (23-24), 1295-1296.
Laurencin et al., "Bone graft substitutes," Expert Review of Medical Devices, 2006, 3(1):49-57.
Laurencin et al., "Regenerative engineering," Science translational medicine, 2012, 4(160): 160ed9, 4 pages.
Laurencin et al., "Tissue engineering: orthopedic applications," Annual review of biomedical engineering, 1999, 1, (1), 19-46.
Madlon-Kay et al., "Too many shots? Parent, nurse, and physician attitudes toward multiple simultaneous childhood vaccinations," Archives of Family Medicine, 1994, 3(7):610-13.
McHugh et al., Fabrication of fillable microparticles and other complex 3D microstructures, Science, 2017, 357(6356):1138-1142.
McHugh et al., "Single-injection vaccines: Progress, challenges, and opportunities," Journal of Controlled Release, 2015, 219:596-609.
Meng et al., "A Hybrid Inductive-Ultrasonic Link for Wireless Power Transmission to Millimeter-Sized Biomedical Implats," IEEE Transactions on Circuits and Systems—II: Express Briefs, 2017, 64(10):1137-1141.
Narayanan et al., "Poly (lactic acid)-based biomaterials for orthopaedic regenerative engineering," Advanced drug delivery reviews, 2016, 107, 247-276.
Nguyen et al., "Piezoelectric nanoribbons for monitoring cellular deformations," Nature Nanotechnology, 2012, 7:587-593.
Poeggel et al., "Optical Fibre Pressure Sensors in Medical Applications," Sensors, 2015, 15(7):17115-17148.
Rolland et al., "Direct fabrication and harvesting of monodisperse, shape-specific nanobiomaterials," Journal of the American Chemical Society, 2005, 127(28):10096-10100.
Sanni et al., "Inductive and Ultrasonic Multi-Tier Interface for Low-Power, Deeply Implantable Medical Devices," IEEE Transactions on Biomedical Circuits and Systems, 2012, 6(4):297-308.
Shende et al., Micro to nanoneedles: a trend of modernized transepidermal drug delivery system, Artificial Cells, Nanomedicine, and Biotechnology, 2017, 8 pages.
Simonelli et al., "Dissolution rates of high energy polyvinylpyrrolidone (PVP)-sulfathiazole coprecipitates," Journal of pharmaceutical sciences, 1969, 58(5):538-549.
Soltman et al., "Inkjet-printed line morphologies and temperature control of the coffee ring effect," Langmuir, 2008, 24(5):2224-2231.
Sullivan et al., "Dissolving polymer microneedle patches for influenza vaccination," Nature medicine, 2010, 16(8):915-921.
Tanimoto et al., "Effect of helix inversion of poly(β-phenethyl l-aspartate) on macroscopic piezoelectricity," Japanese Journal of Applied Physics, 2014, 53(9S):09PC01.
Vaers, Vaccine Adverse Event Reporting System. <https://vaers.hhs.gov/data/index> webpage available as early as Oct. 9, 2009, 2 pages.
Xu et al., "Future of the particle replication in nonwetting templates (PRINT) technology," Angewandte Chemie International Edition, 2013, 52(26):6580-6589.
Yu et al., "Oral fast-dissolving drug delivery membranes prepared from electrospun polyvinylpyrrolidone ultrafine fibers," Nanotechnology, 2009, 20(5):055104, 9 pages.
International Search Report and Written Opinion for Application No. PCT/US2019/020838 dated Jun. 26, 2019 (14 pages).
Ando et al., "Pressure-sensitive touch panel based on piezoelectric poly (I-lactic acid) film", 2013, Jpn. J. Appl. Phys. 52:09KD17.
Bello et al., "Development of a smart pump for monitoring and controlling intraocular pressure", Ann Biomed Eng 45:990-1002, 2017.
Bos et al., "Resorbable poly(L-lactide) plates and screws for the fixation of zygomatic fractures", 1987, J Oral Maxillofac Surg, 45:751-753.
Chee et al., "An investigation of array of piezoelectric transducer for raindrop energy harvesting application", 2016, IEEE Region Tenth Conference, pp. 3771-3774.

(56) References Cited

OTHER PUBLICATIONS

Lee et al., "Micromachined piezoelectric force senors based on PZT thin films", 1996, IEEE Trans Ultrason Farroelectri Freq Control, 43:553-559.
Di Mario et al., "Drug-eluting bioabsorbable magnesium stent", 2004, J Interv Cardiol., 17:391-395.
Fukada, "New Piezoelectric polymers" 1998, Jpn J Appl Phys 37:2775-2780.
Ewald et al., "Monitoring of vital signs for long-term survival of mice under anesthesia", 2011, Cold Spring Harb Protoc. 2011:pdb.prot5563.
Guo et al., "Measurements of piezoelectric coefficient d33 of lead zirconate titanate thin films using a mini force hammer", 2013, J Vib Accoust, 135:011003.
Jayson et al., "Intra-articular pressure in rheumatoid arthritis of the knee 3. Pressure changes during joint use", Ann Rheum Dis, 1970, 29:401-408.
Kang et al., "Bioresorbable silicon electronic sensors for the brain", Nature, 2016, 530:71-76.
Liu et al., "Design and development of three-dimensional scaffolds fortissue engineering", 2007, Chem Eng Res Des, 85:1051-1064.
Maloney et al., "Intracranial pressure monitoring in acute liver failure: Institutional case series", 2016, Neurocrit Care 25:86-93.
Masamichi et al., "Film sensor device fabricated by a piezoelectric poly(L-lactic acid) film", 2012, Jpn J Appl Phys 51:09LD14.
Masamichi et al., "Pressure sensitive touch panel based on piezoelctric poly(L-lactic acid) film", 2013, Jpn J Appl Phys 52:09KD17.
Minary-Jolandan et al., "Nanoscale characterization of isolated individual type I collagen fibrils: Polarization and piezoelectricity", 2009, Nanotechnology 20:085706.
Nguyen et al., "Wafter-scale nanopatterning and translation into high-performance piezoelectric nanowires", 2010, Nano Lett 10: 4595-4599.
Nguyen, et al., "Bionics in tissue engineering" 2017, Tissue Engineering for Artifical Organs, pp. 677-669.
Qi et al., "Enhanced piezoelectricity and stretchability in energy harvesting devices fabricated from buckled PZT ribbons", 2011, Nano Lett. 11:1331-1336.
Qi et al., "Stretchable piezoelectric nanoribbons for biocompatible energy harvesting", Stretchable Electrionics, pp. 111-139.
Ru et al., "Dominant B-form of poly(l-lactic acid) obtained directly from melt under shear and pressure fields", 2016, Macromolecules 49:3826-3837.
Saravanos et al., "Layerwise mechanics and finite element for the dynamic analysis of piezoelectric composite plates", 1997, Int J Solids Struct 34:359-378.
Sawano et al., "New design of actuator using shear piezoelectricity of a chiral polymer, and prototype device", 2010, Polym. Int. 59: 365-370.
Seol et al., "Hysteretic behavior of contact force response in triboelectric nanogenerator", 2017, Nano Energy 32:408-413.
Sinderby et al., "Diaphragm activation during exercise in chronic obstructive pulmonary disease", 2001, Am J Respir Crit Care Med, 163:1637-1641.
Syuhei et al., "Sensing using piezoelectric chiral polymer fiber", 2012, Jpn. J. Appl. Phys. 51:09LD16.
Tajitsu et al., "Microactuators with piezoelectric polylactic acid fibers—toward the realizaation of tweezers for biological cells", 2004, Ferroelectrics 304:195-200.
Talmor et al., "Mechanical ventilation guided by esophageal pressure in acute lung injury", N. Engl. J Med., 2008, 359, 2095-2104.
Xu et al., "Improvements of thermal property and crystallization behavior of PLLA based multiblock copolymer by forming sterocomplexwith PDLA oligomer", 2006, Polymer (Guildf), 47:3922-3928.
Yoshida et al., "High piezoelectric performance of poly (lactic acid) film manufactured by solid state extrusion", 2014, Jpn. J. Appl. Phys. 53:09PC02.
Yoshida et al., "Piezolectric motion of multilayer film with alternate rows of optical isomers of chiral polymer film", 2011, Jpn J Appl Phys 50:09ND13.
Zheng et al., "Biodegradable triboelectric nongenerator as a lifetime designed implantable power source", 2016, Sci Adv 2:e1501478.
Zi et al., "Triboelectric-pyroelectric-piezoelectric hybrid cell for high-efficiency energy-harvesting and self-powered sensing", Adv Mater 27:2340-2347, 2015.
D'Lima et al. "Implantable sensor technology: measuring bone and joint biomechanics of daily life in vivo", Arthritis Reseasrch and Therapy, 2013, 15: 203.
Klosterhoff et al., "Implantable Sensors for Regenerative Medicine", Journal of Biomechanical Engineering, ASME Feb. 2017, vol. 139, 021009-1.
International Preliminary Report on Patentability for Application No. PCT/US2018/022441 dated Sep. 17, 2019 (10 pages).
Zhang et al., "Piezoelectric polymer multilayer on flexible substrate for energy harvesting," IEEE Transactions on Ultrasonics, Ferroelectrics, and Frequency Control, 2013, 60(9):2013-2020.
Ramadan et al., "A review of piezoelectric polymers as functional materials for electromechanical transducers," Smart Materials and Structures 23, 2014, 033001.
Dagdeviren et al., "Recent progress in flexible and stretchable piezoelectric devices for mechanical energy harvesting, sensing and actuation," Extreme Mechanics Letters, 2016, 9(1):269-281.
European Patent Office Extended Search Report for Application No. 18767093.0 dated Nov. 27, 2020 (13 pages).
European Patent Office Extended Search Report for Application No. 19764864 dated Mar. 22, 2022 (11 pages).
Abcam. Elisa kit for MCP-1. https://www.abcam.com/rat-mcpl-elisa-kit-ab219045.html. Accessed Aug. 22, 2022 (5 pages).
Abcam. Elisa kit for TNF-alpha. https://www.abcam.com/rat-tnf-alpha-elisa-kit-ab236712.html. Accessed Aug. 22, 2022 (5 pages).
AFPRO Filters. Pml: The Most Hazardous Kind of Particulate Matter. https://web.archive.org/web/20200609213853/https://www.afprofilters.com/pml-airfilter/, Jun. 9, 2020, (4 pages).
Ager, D. J. et al. Stability of aspirin in solid mixtures. Journal of pharmaceutical sciences 1986, 75, (1), 97-101.
Alemdaroğlu, C.; et al. An investigation on burn wound healing in rats with chitosan gel formulation containing epidermal growth factor. Burns 2006, 32, (3), 319-327.
Alneami AQ, et al. Effect of Electrical Current Stimulation on Pseudomonas Aeruginosa Growth. Journal of Physics: Conference Series. 2018;1003:012112.
Amirnasr, E. et al. Basis Weight Uniformity Analysis in Nonwovens. The Journal of The Textile Institute 2014, 105 (4), 444-453.
Ando et al., "New human machine interface devices using a piezoelectric poly(L-lactic acid) film" in 2013 IEEE International Symposium on the Applications of Ferroelectric and Workshop on the Piezoresponse Force Microscopy (ISAF/PFM) (IEEE, 2013), pp. 236-239.
Arakha M, et al. The effects of interfacial potential on antimicrobial propensity of ZnO nanoparticle. Scientific Reports. 2015;5(1):9578.
Asadi MR, et al. Bacterial Inhibition by Electrical Stimulation. Advances in Wound Care. 2013;3(2):91-97.
Atkins et al. Raman spectroscopy of blood and blood components. Appl. Spectrosc. 71, 767-793 (2017).
Babu, R. et al. Assessment of skin irritation and molecular responses in rat skin exposed to nonane, dodecane and tetradecane. Toxicology letters 2004, 153, (2), 255-266.
Bai, Y.; et al. Washable Multilayer Triboelectric Air Filter for Efficient Particulate Matter Pm2. 5 Removal. Advanced Functional Materials 2018, 28 (15), 1706680.
Baker, B., et al. Electrical stimulation of articular cartilage regeneration. Annals of the New York Academy of Sciences 238, 491-499 (1974).
Banerjee J, et al. Silver-zinc redox-coupled electroceutical wound dressing disrupts bacterial biofilm. PLoS One. 2015; 10(3):e0119531-eOl 19531.
Barbour, K. E.; et al., Prevalence of doctor-diagnosed arthritis and arthritis-attributable activity limitation—United States, 2010-2012. MMWR. Morbidity and mortality weekly report 2013, 62, (44), 869-873.

(56) References Cited

OTHER PUBLICATIONS

Barbour, K. E.; et al., Vital signs: prevalence of doctor-diagnosed arthritis and arthritis-attributable activity limitation—United States, 2013-2015. MMWR. Morbidity and mortality weekly report 2017, 66, (9), 246-253.

Barki KG, et al. Electric Field Based Dressing Disrupts Mixed-Species Bacterial Biofilm Infection and Restores Functional Wound Healing. Ann Surg. 2019;269(4).

Barton, N. J.; et al., Demonstration of a novel technique to quantitatively asses inflammatory mediators and cells in rat knee joints. Journal of Inflammation 2007, 4, (1), 13.

Bastaki, S. M.; ct al. Effect of Aspirin and ibuprofen either alone or in combination on gastric mucosa and bleeding time and on serum prostaglandin E 2 and thromboxane A 2 levels in the anaesthetized rats in vivo. Molecular and cellular biochemistry 2018, 438, (1-2), 25-34.

Baur D, Gladstone BP, Burkert F, Carrara E, Foschi F, Dobele S, Tacconelli E: Effect of antibiotic stewardship on the incidence of infection and colonisation with antibiotic-resistant bacteria and Clostridium difficile infection: a systematic review and meta-analysis. Lancet Infect Dis 2017, 17(9): 990-1001.

BCC Research—Global Markets for Drug-Device Combinations, Jan. 2015. PHM045D.

Beaudet J, Tulman ER, Pflaum K, Liao X, Kutish GF, Szczepanek SM, Silbart LK, Geary SJ: Transcriptional Profiling of the Chicken Tracheal Response to Virulent Mycoplasma galliscpticum Strain Rlow. Infect Immun 2017, 85(10).

Bergsma JE, et al. Late degradation tissue response to poly(l-lactide) bone plates and screws. Biomaterials. 1995;16(1):25-31.

Besinis, A.; et al. Antibacterial activity and biofilm inhibition by surface modified titanium alloy medical implants following application of silver, titanium dioxide and hydroxyapatite nanocoatings. Nanotoxicology 2017, 11,(3), 327-338.

Bir SC, et al. Control of angiogenesis dictated by picomolar superoxide levels. Free Radic Biol Med. 2013;63:135-142.

Blake KM, Carrigan SO, Issekutz AC, Stadnyk AW: Neutrophils migrate across intestinal epithelium using beta2 integrin (CD1 lb/CD18)-independent mechanisms. Clin Exp Immunol 2004, 136(2):262-268.

Bloomberg News. Mask Mandates by Nation: Most Still Awaits a Breath of Fresh Air. https://www.bloomberg.com/news/articles/2021-05-14/mask-mandates-by-nation-most-still-await-a-breath-of-fresh-air. May 14, 2021 (9 pages).

Boks NP, et al. Forces involved in bacterial adhesion to hydrophilic and hydrophobic surfaces. Microbiology. 2008;154(Pt 10):3122-3133.

Bose, S.; et al. A review on advances of sustained release drug delivery system. Int. Res. J. Pharm 2013, 4,1-4.

Boster Bio. ELISA kit for IL-1 alpha, https://www.bosterbio.com/rat-il-1-alpha-picokine-trade-elisa-kit-ek0390-boster.html#bs_references. Jul. 1, 2013. Accessed on Aug. 22, 2022. (8 pages).

Bottino, M. C. et al. in Biomaterials for Oral and Craniomaxillofacial Applications vol. 17 90-100 (Karger Publishers, 2015).

Boutry et al., A stretchable and biodegradable strain and pressure sensor for orthopaedic application. Nat. Electron. 1, 314-321 (2018).

Boutry et al., Biodegradable and flexible arterial-pulse sensor for the wireless monitoring of blood flow. Nat. Biomed. Eng. 3, 47-57 (2019).

Bronaugh, R. L.; et al., Differences in permeability of rat skin related to sex and body site. J. Soc. Cosmet. Chem 1983, 34, (12), 127-135.

Brooks, J. T.; et al., Effectiveness of Mask Wearing to Control Community Spread of Sars-Cov-2. Jama 2021, 325 (10), 998-999.

Brune, K.; et al., Recent Insight into the Mechanism of Gastrointestinal Tract Ulceration. Scandinavian Journal of Rheumatology 1987, 16 (sup65), 135-140.

Byrne, J. D.; et al.. Injection Molded Autoclavable, Scalable, Conformable (Imasc) System for Aerosol-Based Protection: A Prospective Single-Arm Feasibility Study. BMJ open 2020, 10 (7), e039120.

Caballe-Serrano, J. et al. On the search of the ideal barrier membrane for guided bone regeneration. Journal of clinical and experimental dentistry 10, e477 (2018).

Cadavid, A. P., Aspirin: the mechanism of action revisited in the context of pregnancy complications. Frontiers in immunology 2017, 8, 261.

Campbell, C. L. et al. Aspirin dose for the prevention of cardiovascular disease: a systematic review. Jama 2007, 297,(18), 2018-2024.

Carvalho, E. O. et al. "Tailoring bacteria response by piezoelectric stimulation." ACS applied materials & interfaces 11.30 (2019): 27297-27305.

Caspani, M. Delta Variant Pushes Us Cases Hospitalizations 6 Month High. Aug. 9, 2021. https://web.archive.org/web/20210809174911/https://www.reuters.com/world/us/delta-variant-pushes-us-cases-hospitalizations-6-month-high-2021-08-09/ (12 pages).

CDC. Antibiotic resistance threats in the United States, 2019. US Department of Health and Human Services. 2019 (150 pages).

CDC. Implementing Filtering Facepiece Respirator (Ffr) Reuse, Including Reuse after Decontamination, When There Are Known Shortages of N95 Respirators. https://www.cdc.gov/coronavirus/2019-ncov/hcp/ppe-strategy/decontamination-reuse-respirators.html, Oct. 19, 2020, (10 pages).

CDC. Periodontal Disease. <https://www.cdc.gov/oralhealth/conditions/periodontal-disease.html.> (Jul. 10, 2013).

CDC. Personal Protective Equipment: Questions and Answers, https://www.cdc.gov/coronavirus/2019-ncov/hcp/respirator-use-faq.html (Apr. 9, 2021) (6 pages).

Chang et al., Biodegradable electronic systems in 3D, heterogeneously integrated formats. Adv. Mater. 30, 1704955 (2018).

Chatterjee, A.; et al., In vitro and in vivo comparison of dermal irritancy of jet fuel exposure using EpiDerm™(EPI-200) cultured human skin and hairless rats. Toxicology letters 2006, 167, (2), 85-94.

Chen, C.-C.; et al. Aerosol Penetration through Surgical Masks. American journal of infection control 1992, 20 (4), 177-184.

Chen, M.-C et al. Implantable polymeric microneedles with phototriggerable properties as a patient-controlled transdermal analgesia system. Journal of Materials Chemistry B 2017, 5, (3), 496-503.

Cheng, Y.; et al. Face Masks Effectively Limit the Probability of Sars-Cov-2 Transmission. Science 2021 1439-1443.

Choi, S.; et al. Biodegradable, Efficient, and Breathable Multi-Use Face Mask Filter. Advanced Science 2021, 8 (6), 2003155.

Chorsi MT, et al. Piezoelectric Biomaterials for Sensors and Actuators. Advanced Materials. 2019;31(1):1802084.

Chu et al., "Piezoelectric stimulation by ultrasound faciliates chondrogenesis of mesenchymal stem cells", J Acoustical Society of American, 2020, vol. 148, No. 1, pp. EL58-EL64.

Chu, D. K.; et al. Physical Distancing, Face Masks, and Eye Protection to Prevent Person-to-Person Transmission of Sars-Cov-2 and Covid-19: A Systematic Review and Meta-Analysis. The lancet 2020, 395 (10242), 1973-1987.

Chu, J.; et al. Thinking Green: Modelling Respirator Reuse Strategies to Reduce Cost and Waste. BMJ open 2021, 11 (7), e048687.

Clearfield, D. S., et al. Osteochondral Differentiation of Fluorescent Multireporter Cells on Zonally-Organized Biomaterials. Tissue Engineering Part A 25,468-486 (2019).

Cohen, A. J.; et al. Estimates and 25-Year Trends of the Global Burden of Disease Attributable to Ambient Air Pollution: An Analysis of Data from the Global Burden of Diseases Study 2015. The Lancet 2017,389 (10082), 1907-1918.

Combe, R.; et al. The monosodium iodoacetate model of osteoarthritis: a model of chronic nociceptive pain in rats? Neuroscience letters 2004, 370, (2-3), 236-240.

Cooper MA, et al. Fix the antibiotics pipeline. Nature. 2011; 472(7341):32-32.

Creech et al., "Prevention of Recunent Staphylococcal Skin Infections," Infect Dis Clin North Am. Sep. 2015; 29(3): 429-464.

Crofford, L. J.. Use of NSAIDs in treating patients with arthritis. Arthritis research & therapy 2013, 15, (3), S2 (10 pages).

Crone S, et al. A novel in vitro wound biofilm model used to evaluate low-frequency ultrasonic-assisted wound debridement. J Wound Care 2015;24(2):64-72.

(56) References Cited

OTHER PUBLICATIONS

Cui, et al. Study on a piezoelectric micropump for the controlled drug delivery system. Microfluid. Nanofluidics 3, 377-390 (2007).
Curdy, C. et al. Piroxicam delivery into human stratum corneum in vivo: iontophoresis versus passive diffusion. Journal of Controlled Release 2001, 76, (1-2), 73-79.
Curry EJ, et al. Biodegradable nanofiber-based piezoelectric transducer. Proceedings of the National Academy of Sciences. 2020;117(1):214-220.
Curry, E. J.; et al. 3D nano-and micro-patterning of biomaterials for controlled drug delivery. Therapeutic Delivery 2016.
Da Silva et al., Biocompatibility, biodegradation and excretion of polylactic acid (PLA) in medical implants and theranostic systems. Chem. Eng. J. 340, 9-14 (2018).
Daeschlein G, et al. Antibacterial activity of positive and negative polarity low-voltage pulsed current (LVPC) on six typical Gram-positive and Gram-negative bacterial pathogens of chronic wounds. Wound Repair Regen. 2007;15(3):399-403.
Dagdeviren C, et al. Conformable amplified lead zirconate titanate sensors with enhanced piezoelectric response for cutaneous pressure monitoring. Nature Communications. 2014;5(1):4496.
Dagdeviren C, et al. Conformal piezoelectric energy harvesting and storage from motions of the heart, lung, and diaphragm. Proceedings of the National Academy of Sciences. 2014; 111(5): 1927.
Das, R. et al., Biodegradable Nonfiber Bone-Tissue Scaffold as Remotely-Controlled and Self-Powering Electrical Stimulator. Nano Energy 2020, 105028.
Davidson, C. I.; et al. Airborne Particulate Matter and Human Health: A Review. Aerosol Science and Technology 2005, 39 (8), 737-749.
Degenhart et al., Histological evaluation of a clironically-implanted electrocorticographic electrode grid in a non-human primate. 13, 046019 (2016).
Deleo et al., "Reemergence of antibiotic-resistant Staphylococcus aureus in the genomics era," JCL, 2009,119, 2464-2474.
Deleo FR, Diep BA, Otto M: Host defense and pathogenesis in *Staphylococcus aureus* infections. Infect Dis Clin North Am 2009, 23(l):17-34.
Derakhshandeh H, et al. A Wirelessly Controlled Smart Bandage with 3D-Printed Miniaturized Needle Arrays. Adv Funct Mater. 2020;30(13): 1905544.
Desai, T. A.; et al., Nanoporous implants for controlled drug delivery. In BioMEMS and Biomedical Nanotechnology, Springer: 2006; pp. 263-286.
Dimitroulas, T.; et al. In Biologic drugs as analgesics for the management of osteoarthritis, Seminars in arthritis and rheumatism, 2017; Elsevier pp. 687-691.
Dixon, W. J. et al. A method for obtaining and analyzing sensitivity data. Journal of the American Statistical Association 1948, 43, (241), 109-126.
Dominguez, C. A. et al. Sex differences in the development of localized and spread mechanical hypersensitivity in rats after injury to the infraorbital or sciatie nerves to create a model for neuropathic pain. Gender medicine 2009, 6, 225-234.
Dong P-T, et al. Photolysis of Staphyloxanthin in Methicillin-Resistant *Staphylococcus aureus* Potentiates Killing by Reactive Oxygen Species. Advanced Science. 2019;6(11):1900030.
Donnelly, R. F.; et al. Hydrogel-forming microneedle arrays for enhanced transdermal drug delivery. Advanced functional materials 2012, 22, (23), 4879-4890.
Draize, J. H. et al. Methods for the study of irritation and toxicity of substances applied topically to the skin and mucous membranes. Journal of pharmacology and Experimental Therapeutics 1944, 82, (3), 377-390.
Dwyer DJ, et al. Antibiotics induce redox-related physiological alterations as part of their lethality. Proceedings of the National Academy of Sciences of the United States of America. 2014;111(20):E2100-2109.

Englander L, et al. Nitric oxide nanoparticle technology: a novel antimicrobial agent in the context of current treatment of skin and soft tissue infection. J Clin Aesthet Dermatol. 2010;3(6):45-50.
Eppley BL, et al. Degradation characteristics of PLLA-PGA bone fixation devices. The Journal of craniofacial surgery. 1997;8(2): 116-120.
Esposito S, et al. Antimicrobial Treatment of *Staphylococcus aureus* in Patients With Cystic Fibrosis. Front Pharmacol. 2019;10:849-849.
European Patent Office Partial Search Report for U.S. Appl. No. 19/764,864 dated Dec. 21, 2021 (12 pages).
Farah et al. Physical and mechanical properties of PLA, and their functions in widespread application—a comprehensive review. Adv. Drug Deliv. Rev. 107, 367-392 (2016).
FDA. N95 Respirators, Surgical Masks, and Face Masks, https://www.fda.gov/medical-devices/personal-protective-equipment-infection-control/n95-respirators-surgical-masks-face-masks-and-barrier-face-coverings Last updated Jul. 19, 2022 (6 pages).
Feng, Y. et al. Engineering Spherical Lead Zirconate Titanate to Explore the Essence of Piezo-Catalysis. Nano Energy 2017, 40, 481-486.
Feng, Y.; et al. Self-Powered Electrostatic Filter with Enhanced Photocatalytic Degradation of Formaldehyde Based on Built-in Triboelectric Nanogenerators. ACS nano 2017, 11 (12), 12411-12418.
Formenti, D.; et al. Thermal imaging of exercise-associated skin temperature changes in trained and untrained female subjects. Annals of biomedical engineering 2013, 41, (4), 863-871.
Fosslien, E., Adverse effects of nonsteroidal anti-inflammatory drugs on the gastrointestinal system. Annals of Clinical & Laboratory Science 1998,28, (2), 67-81.
Foti JJ, et al. Oxidation of the Guanine Nucleotide Pool Underlies Cell Death by Bactericidal Antibiotics. Science. 2012;336(6079):315-319.
Freeman J, et al. Comparison of the efficacy of ramoplanin and vancomycin in both in vitro and in vivo models of clindamycin-induced Clostridium difficile infection. J Antimicrob Chemother. 2005;56(4):717-725.
Friebe, M.; et al. Synovial distribution of "systemically" administered acetylsalicylic acid in the isolated perfused equine distal limb. BMC veterinary research 2013, 9, (1), 56.
Frim, J. et al. Body composition and skin temperature variation. Journal of Applied Physiology 1990, 68, (2), 540-543.
Fu, C.-H. J. et al. Method for determination of aspirin and salicylic acid in rat whole blood by high pressure liquid chromatography. Analytical Letters 1985, 18, (3), 269-277.
Gabriel D, et al. A photo-triggered layered surface coating producing reactive oxygen species. Biomaterials. 2013;34(38): 9763-9769.
Gao, Q., et al. Ultrasound Stimulation of Different Dental Stem Cell Populations: Role of Mitogen-activated Protein Kinase Signaling. J. Endod. 42, 2016, 425-431.
Garland MJ(1), Migalska K, Mahmood TM, Singh TR, Woolfson AD, Donnelly RF. Microneedle arrays as medical devices for enhanced transdermal drug delivery Expert Rev Med Devices. Jul. 2011;8(4):459-82.
Gentile, P. et al. An overview of poly (lactic-co-glycolic) acid (PLGA)-based biomaterials for bone tissue engineering. International journal of molecular sciences 2014, 15, (3), 3640-3659.
Gibaldi, M. et al. Bioavailability of aspirin from commercial suppositories. Journal of pharmaceutical sciences 1975, 64, (6), 1064-1066.
Gohil, S. V. et al. Spatially controlled rhBMP-2 mediated calvarial bone formation in a transgenic mouse model. International journal of biological macromolecules 2018, 106, 1159-1165.
Golabchi et al., Melatonin improves quality and longevity of chronic neural recording. 180, 225-239 (2018).
Gordon CP, Williams P, Chan WC: Attenuating *Straphylococcus aureus* virulence gene regulation: a medicinal chemistry perspective. J Med Chem 2013, 56(4):1389-1404.
Gottlieb, H. E.; et al. Nmr Chemical Shifts of Common Laboratory Solvents as Trace Impurities. Journal of Organic Chemistiy 1997, 62 (21), 7512-7515.

(56) References Cited

OTHER PUBLICATIONS

Grant SS, et al. Eradication of bacterial persisters with antibiotic-generated hydroxyl radicals. Proceedings of the National Academy of Sciences. 2012;109(30):12147.
Grassi, M.; et al. Mathematical modelling and controlled drug delivery: matrix systems. Current drug delivery 2005, 2,(1), 97-116.
Gu, G. Q. et al. Triboelectric Nanogenerator Enhanced Nanofiber Air Filters for Efficient Particulate Matter Removal. Acs Nano 2017, 11 (6), 6211-6217.
Guerin et al., Control of piezoelectricity in amino acids by supramolecular packing. Nat. Mater. 17, 180-186 (2018).
Guo, H.; et al. A pure zinc membrane with degradability and osteogenesis promotion for guided bone regeneration: in vitro and in vivo studies. Acta Biomater. 2020, 396-409.
Gurung, D. et al. Transient temperature distribution in human dermal part with protective layer at low atmospheric temperature. International Journal of Biomathematics 2010, 3, (04), 439-451.
Gustafsson, M. et al. Pain, coping and analgesic medication usage in rheumatoid arthritis patients. Patient education and counseling 1999, 37, (1), 33-41.
Gutarowska, B., et al. "PLA Nonwovens modified with poly (dimethylaminoethyl methacrylate) as antimicrobial filter materials for workplaces." Textile Research Journal 85.10 (2015): 1083-1094.
Haddadin et al., "Methicillin resistant *Staphylococcus aureus* (MRSA) in the intensive care unit," Postgraduate Medical Journal 2002; 78:385-392.
Hasuike A, et al. In vivo bone regenerative effect of low-intensity pulsed ultrasound in rat calvarial defects. Oral Surgery, Oral Medicine, Oral Pathology, Oral Radiology, and Endodontology. 2011;111(1):e12-e20.
Hauert AB, Martinelli S, Marone C, Niggli V: Differentiated HL-60 cells are a valid model system for the analysis of human neutrophil migration and chemotaxis. Int J Biochem Cell Biol 2002, 34(7): 838-854.
He, M. et al. Intradermal implantable PLGA microneedles for etonogestrel sustained release. Journal of Pharmaceutical Sciences 2020, 1958-1966.
He, Z. et al. An overview of hydrogel-based intra-articular drug delivery for the treatment of osteoarthritis. Colloids and Surfaces B: Biointerfaces 2017, 154, 33-39.
Hickey, D.J., et al. Electrophoretic deposition of MgO nanoparticles imparts antibacterial properties to poly-L-lactic acid for orthopedic applications. Journal of Biomedical Materials Research Part A, 2017, 105(11), 3136-3147.
Hong K-S, et al. Piezoelectrochemical Effect: A New Mechanism for Azo Dye Decolorization in Aqueous Solution through Vibrating Piezoelectric Microfibers. The Journal of Physical Chemistry C. 2012; 116(24): 13045-13051.
Horodyckid et al., Safe long-term repeated disruption of the blood-brain barrier using an implantable ultrasound device: A multiparametric study in a primate model. J. Neurosurg. 126, 1351-1361 (2017).
Hossain, E.; et al. Recharging and Rejuvenation of Decontaminated N95 Masks. Physics of Fluids 2020, 32 (9), 093304.
Howard, J.; et al, An Evidence Review of Face Masks against Covid-19. Proceedings of the National Academy of Sciences 2021, 118 (4).
Hu H, et al. Stretchable ultrasonic transducer arrays for three-dimensional imaging on complex surfaces. Science Advances. 2018;4(3):caar3979.
Huang, X.; et al. On the importance and mechanisms of burst release in matrix-controlled drug deliveiy systems. Journal of controlled release 2001,73, (2-3), 121-136.
Hui J, et al. Photo-Disassembly of Membrane Microdomains Revives Conventional Antibiotics against MRSA. Advanced Science. 2020:7(6): 1903117.
Iati, M. More Experts Now Recommend Medical Masks. Good Ones Are Hard to Find. Feb. 2, 2021. https://www.washingtonpost.com/health/2021/02/02/medical-mask-shortage/ (4 pages).
IDATA Reasearch. 2017 US Dental Barrier Membrane Market Driven by Increased Use of Resorbable Membranes. https://idataresearch.com/2017-us-dental-barrier-membrane-market-driven-increased-use-resorbable-membranes/. Nov. 10, 2017. (6 pages).
Idbaih et al., Safety and feasibility of repeated and transient blood-brain barrier disruption by pulsed ultrasound in patients with recurrent glioblastoma. Clin. Cancer Res. 25, 3793-3801 (2019).
Ikada et al. Enhancement of bone formation by drawn poly(L-lactide). J. Biomed. Mater. Res. 30, 553-558 (1996).
Indian Office Action for Application 202037042930 dated Jun. 20, 2022 (6 pages).
Infection Control Today, "New Research Estimates MRSA Infections Cost U.S. Hospitals $3.2 Billion to $4.2 Billion Annually," <https://www.infectioncontroltoday.com/view/new-research-estimates-mrsa-infections-cost-us-hospitals-32-billion-42-billion-annually> dated May 16, 2005.
Institute of Medicine of the National Academies. Characteristics of Respirators and Medical Masks. In Reusability of Facemasks During an Influenza Pandemic: Facing the Flu, 2006; pp. 22-42.
International Preliminary Report on Patentability for Application No. PCT/US2021/021677 dated Sep. 6, 2022 (11 pages).
International Search Report and Written Opinion for Application No. PCT/US21/53887 dated Jan. 28, 2022 (14 pages).
Jacobi, U. et al. Porcine ear skin: an in vitro model for human skin. Skin Research and Technology 2007, 13, (1), 19-24.
Ji, W. et al. Incorporation of stromal cell-derived factor-1α in PCL/gelatin electrospun membranes for guided bone regeneration. Biomaterials 34, 735-745 (2013).
Jin Y, Li M, Shang Y, Liu L, Shen X, Lv Z, Hao Z, Duan J, Wu Y, Chen C et al.: Sub-Inhibitory Concentrations of Mupirocin Strongly Inhibit Alpha-Toxin Production in High-Level Mupirocin-Resistant MRSA by Down-Regulating agr, saeRS, and sarA. Front Microbiol 2018, 9:993.
Jung, Y.-s et al. Thermo-sensitive injectable hydrogel based on the physical mixing of hyaluronic acid and Pluronic F-127 for sustained NSAID delivery. Carbohydrate polymers 2017, 156, 403-408.
Jüni, P.; et al. Intra-articular corticosteroid for knee osteoarthritis. Cochrane Database of Systematic Reviews 2015, (10) (81 pages).
Kalali Y, Haghighat S. Mahdavi M: Passive immunotherapy with specific IgG fraction against autolysin: Analogous protectivity in the MRSA infection with antibiotic therapy. Immunol Lett 2019, 212:125-131.
Kaushik, S. et al. Lack of pain associated with microfabricated microneedles. Anesthesia & Analgesia 2001, 92, (2), 502-504.
Kean, T.; et al. Biodegradation, Biodistribution and Toxicity of Chitosan. Advanced drug delivery reviews 2010, 62(1), 3-11.
Kern, H., et al. Recovery of long-term denervated human muscles induced by electrical stimulation. Muscle & nerve 31, 98-101 (2005).
Khalid, B.; et al.. Direct Blow-Spinning of Nanofibers on a Window Screen for Highly Efficient Pm2. 5 Removal. Nano letters 2017, 17 (2), 1140-1148.
Khanal, M.; et al. Injectable nanocomposite analgesic delivery system for musculoskeletal pain management. Acta biomaterialia 2018, 74, 280-290.
Kim, D.-H et al. Sustained release of dexamethasone from hydrophilic matrices using PLGA nanoparticles for neural drug delivery. Biomaterials 2006, 27, (15), 3031-3037.
Kinoshita, N. et al. Noninvasive localized delivery of Herceptin to the mouse brain by MRI-guided focused ultrasound-induced bloodbrain barrier disruption. Proc. Natl. Acad. Sci. U.S.A. 103, 11719-11723 (2006).
Klein et al., "National Costs Associated with Methicillin-Susceptible and Methicillin-Resistant *Staphylococcus aureus* Hospitalizations in the United States, 2010-2014," Clinical Infectious Diseases, vol. 68, Issue 1, Jan. 1, 2019, pp. 22-28.
Kloth, L. C. Electrical stimulation for wound healing: a review of evidence from in vitro studies, animal experiments, and clinical trials. The international journal of lower extremity wounds 4, 23-44 (2005).
Kobayashi, et al. Label-free imaging of melanoma with confocal photothermal microscopy: Differentiation between malignant and benign tissue. Bioeng. 5, 67 (2018) (18 pages).
Kohanski Ma, et al. A Common Mechanism of Cellular Death Induced by Bactericidal Antibiotics. Cell. 2007;130(5):797-810.

(56) References Cited

OTHER PUBLICATIONS

Kozai et al., Chronic tissue response to carboxymethyl cellulose based dissolvable insertion needle for ultra-small neural probes. 35, 9255-9268 (2014).

Krasowska A, et al. How microorganisms use hydrophobicity and what does this mean for human needs? Front Cell Infect Microbiol. 2014;4:112-112.

Kullenberg, B et al. Intraarticular corticosteroid injection pain relief in osteoarthritis of the hip? The Journal of rheumatology 2004, 31, (11), 2265-2268.

Latimer, J. M. el al. Microwave Oven Irradiation as a Method for Bacterial Decontamination in a Clinical Microbiology Laboratory. Journal of Clinical Microbiology 1977, 6 (4), 340-342.

Laurencin, C. T.; et al. Delivery of small molecules for bone regenerative engineering: preclinical studies and potential clinical applications. Drug discovery today 2014, 19, (6), 794-800.

Lausen M, Pedersen MS, Rahman NSK, Holm-Nielsen LT, Farah FYM, Christiansen G, Birkelund S: Opsonophagocytosis of Chlamydia pneumoniae by Human Monocytes and Neutrophilis, Infect Immun 2020, 88(7).

Leatherby, L. As Covid Cases Rise All over U.S., Lower Vaccination Rates Point to Worse Outcomes. Jul. 31, 2021. https://www.nytimes.com/interactive/2021/07/31/us/covid-delta-cases-deaths.html?action=click&module=Spotlight&pgtype=Homepage (3 pages).

Lee et al., Lactic acid assisted fabrication of bioactive three-dimensional PLLA/β-TCP fibrous scaffold for biomedical application. Chem. Eng. J. 347, 771-781 (2018).

Lee, et al. Piezoelectric properties of electrospun poly(L-lactic acid) nanofiber web. Mater. Lett. 148, 58-62 (2015).

Leung, L. et al. Comparison of morphology and mechanical properties of PLGA bioscaffolds. Biomedical Materials 2008, 3, (2), 025006.

Lewin et al., Free serum haemoglobin is associated with brain atrophy in secondary progressive multiple sclerosis. Wellcome Open Res. 1, 10 (2016) (23 pages).

Lewitus, S. et al. The Effect of Nanoclays on the Properties of PLLA-modified Polymers Part 1: Mechanical and Thermal Properties. Journal of Polymers and the Environment 14, 171-177 (2006).

Li J, et al. Evaluation of Ultrasound-Induced Damage to *Escherichia coli* and *Staphylococcus aureus* by Flow Cytometry and Transmission Electron Microscopy. Appl Environ Microbiol. 2016;82(6):1828-1837.

Li Z, et al. Using Positively Charged Magnetic Nanoparticles to Capture Bacteria at Ultralow Concentration. Nanoscale Research Letters. 2019;14(1):195 (8 pages).

Li, C. et al. Dual-mode operation of flexible piezoelectric polymer diaphragm for intracranial pressure measurement. Appl. Phys. Lett. 96, 053502 (2010).

Li, H. et al. Enhancing the Mechanical Properties of Electrospun Nanofiber Mats through Controllable Welding at the Cross Points. Macromolecular rapid communications 2017, 38 (9), 1600723.

Li, N.; et al. A Work Group Report on Ultrafine Particles (American Academy of Allergy, Asthma & Immunology): Why Ambient Ultrafine and Engineered Nanoparticles Should Receive Special Attention for Possible Adverse Health Outcomes in Human Subjects. Journal of Allergy and Clinical Immunology 2016, 138 (2), 386-396.

Li, P. et al. Air Filtration in the Free Molecular Flow Regime: A Review of High-Efficiency Particulate Air Filters Based on Carbon Nanotubes. Small 2014, 10 (22), 4543-4561.

Li, P. et al. Apatite formation induced by silica gel in a simulated body fluid. Journal of the American Ceramic Society 1992, 75, (8), 2094-2097.

Li, Q. et al. Involvement of the spinal NALP1 inflammasome in neuropathic pain and aspirin-triggered-15-epi-lipoxin A4 induced analgesia. Neuroscience 2013, 254, 230-240.

Li, W. et al. Rapidly separable microneedle patch for the sustained release of a contraceptive. Nature Biomedical Engineering 2019, 3,(3), 220-229.

Li, W.; et al. Long-acting reversible contraception by effervescent microneedle patch. Science advances 2019, 5, (11), eaaw8145.

Liao, L.; et al. Can N95 Respirators Be Reused after Disinfection? How Many Times? ACS nano 2020, 14 (5), 6348-6356.

Liu, C.; et al. Transparent Air Filter for High-Efficiency Pm 2.5 Capture Nature communications 2015, 6 (1), 1-9.

Liu, G. et al. Self-Powered Electrostatic Adsorption Face Mask Based on a Triboelectric Nanogenerator. ACS applied materials & interfaces 2018, 10 (8), 7126-7133.

Liu, H. et al. High-Performance Pm0. 3 Air Filters Using Self-Polarized Electret Nanofiber/Nets. Advanced Functional Materials 2020, 30 (13), 1909554.

Liu, X. et al. A biodegradable multifunctional nanofibrous membrane for periodontal tissue regeneration. Acta Biomater. 2020, 108, 207-222.

Liu, Z.; et al. Understanding the Factors Involved in Determining the Bioburdens of Surgical Masks. Annals of translational medicine 2019, 7 (23).

Lo, K. et al. Small-molecule based musculoskeletal regenerative engineering. Trends in biotechnology 2014, 32, (2), 74-81.

Lobritz MA, et al. Antibiotic efficacy is linked to bacterial cellular respiration. Proceedings of the National Academy of Sciences of the United States of America. 2015;112(27):8173-8180.

Lokuta MA, Nuzzi PA, Huttenlocher A: Analysis of neutrophil polarization and chemotaxis. Methods Mol Biol 2007, 412:211-229.

Long Y, et al. Effective Wound Hearing Enabled by Discrete Alternative Electric Fields from Wearable Nanogenerators. ACS Nano. 2018;12(12):12533-12540.

Lops, C.; et al. Sonophotocatalytic Degradation Mechanisms of Rhodamine B Dye Via Radicals Generation by Micro-and Nano-Particles of Zno. Applied Catalysis B: Environmental 2019, 243, 629-640.

Lu, W.-C et al. Effect of magnesium on the osteogenesis of normal human osteoblasts. Magnes. Res. 30,42-52 (2017).

Lu, X.; et al. Theoretical analysis of calcium phosphate precipitation in simulated body fluid. Biomaterials 2005, 26, (10), 1097-1108.

Ludwig, The velocity of sound through tissues and the acoustic impedance of tissues. The journal of the acoustical society of America 22, 862-866 (1950).

Lundgren, D., et al. "The use of a new bioresorbable barrier for guided bone regeneration in connection with implant installation. Case reports." Clinical Oral Implants Research 5.3 (1994): 177-184.

Luque-Agudo V, et al. Aging of Solvent-Casting PLA-Mg Hydrophobic Films: Impact on Bacterial Adhesion and Viability. Coatings. 2019;9(12) 814.

Luzuriaga MA(1), Berry DR, Reagan JC, Smaldone RA, Gassensmith JJ. Biodegradable 3D printed polymer microneedles for transdermal drug delivery. Lab Chip. Apr. 17, 2018;18(8):1223-1230.

Lv, D.; et al. Ecofriendly Electrospun Membranes Loaded with Visible-Light-Responding Nanoparticles for Multifunctional Usages: Highly Efficient Air Filtration, Dye Scavenging, and Bactericidal Activity. ACS applied materials & interfaces 2019, 11 (13), 12880-12889.

Mahdavi, A. et al. Particle Loading Time and Humidity Effects on the Efficiency of an N95 Filtering Facepiece Respirator Model under Constant and Inhalation Cyclic Flows. Annals of Occupational Hygiene 2015, 59 (5), 629-640.

Manoukian, M. A. C. et al. Topical administration of ibuprofen for injured athletes: considerations, formulations, and comparison to oral delivery. Sports medicine-open 2017, 3, (1), 36, 1-9.

Marzoli, F. et al. Long-lasting, antinociceptive effects of pH-sensitive niosomes loaded with ibuprofen in acute and chronic models of pain. Pharmaceutics 2019,11, (2), 62, 1-12.

McAllister DV(1), Wang PM, Davis SP, Park JH, Canatella PJ, Allen MG, Prausnitz MR. Microfabricated needles for transdermal delivery of macromolecules and nanoparticles: fabrication methods and transport studies. Proc Natl Acad Sci U S A. Nov. 25, 2003;100(24):13755-60.

McCrudden, M. T. et al. Design and physicochemical characterisation of novel dissolving polymeric microneedle arrays for transdermal delivery of high dose, low molecular weight drugs. Journal of Controlled Release 2014, 180, 71-80.

(56) References Cited

OTHER PUBLICATIONS

McDannold, et al. MRI-guided targeted blood-brain barrier disruption with focused ultrasound: Histological findings in rabbits. Ultrasound Med. Biol. 31, 1527-1537 (2005).

Meylan S, et al. Targeting Antibiotic Tolerance, Pathogen by Pathogen. Cell. 2018;172(6):1228-1238.

Middleton, J. C.; Tipton, A. J., Synthetic Biodegradable Polymers as Orthopedic Devices. Biomaterials 2000, 21 (23), 2335-2346.

Mihai MM, et al. Nanomaterials for Wound Healing and Infection Control. Materials (Basel). 2019;12(13):2176.

Millius A, Weiner OD: Chemotaxis in neutrophil-like HL-60 cells. Methods Mol Biol 2009, 571:167-177.

Moga, K. A. et al. Rapidly—dissolvable microneedle patches via a highly scalable and reproducible soft lithography approach. Advanced Materials 2013, 25, (36), 5060-5066.

Mohseni et al., "Gellan gel comprising short PVDF based-nanofibers: The effect of piezoelectric nanofiber on the mechanical and electrical behavior," Materialstoday Communications, vol. 26, Mar. 2021, 101785.

Monsen T, et al. In Vitro Effect of Ultrasound on Bacteria and Suggested Protocol for Sonication and Diagnosis of Prosthetic Infections. J Clin Microbiol. 2009;47(8):2496-2501.

Montgomery CP, Boyle-Vavra S, Daum RS: Importance of the global regulators Agr and SaeRS in the pathogenesis of CA-MRSA USA300 infection. PLoS One 2010, 5(12):e15177.

Morel CM, et al. Stoking the antibiotic pipeline. BMJ. 2010;340:1115-1118.

Nair, L. S.; et al. Polymers as biomaterials for tissue engineering and controlled drug delivery, In Tissue engineering I, Springer: 2005; pp. 47-90.

Najdovski, L. et al. The Killing Activity of Microwaves on Some Non-Sporogenic and Sporogenic Medically Important Bacterial Strains. Journal of Hospital Infection 1991, 19 (4), 239-247.

Nasajpour, A. et al. A multifunctional polymeric periodontal membrane with osteogenic and antibacterial characteristics. Adv. Funct. Mater. 28, 1703437 (2018).

Nazir, M. A. Prevalence of periodontal disease, its association with systemic diseases and prevention. International journal of health sciences 11, 72 (2017), 72-80.

Neely RM, et al. Recent advances in neural dust: towards a neural interface platform. Current Opinion in Neurobiology. 2018;50:64-71.

Nguyen, "A novel injectable piezoelectric hydrogel for osteoarthritis treatment," NIH Project No. 1R21AR074645-01, Award notice date: Apr. 23, 2019, Project Start Date: Jun. 1, 2019 <https://reporter.nih.gov/project-details/9651964> (3 pages).

Nicosia, A., et al. "Air filtration and antimicrobial capabilities of electrospun PLA/PHB containing ionic liquid." Separation and Purification Technology 154 (2015): 154-160.

Nielsen A, Mansson M, Bojer MS, Gram L, Larsen TO, Novick RP, Frees D, Frokiaer H, Ingmer H: Solonamide B inhibits quorum sensing and reduces Staphylococcus aureus mediated killing of human neutrophils. PLoS One 2014, 9(l):e84992.

Noguchi, Y. Why N95 Masks Are Stil in Short Supply in the U.S. https://www.npr.org/sections/health-shots/2021/01/27/960336778/why-n95-masks-are-still-inshort-supply-in-the-u-s, Jan. 27, 2021 (17 pages).

Norman, J. J.; et al. Microneedle patches: usability and acceptability for self-vaccination against influenza. Vaccine 2014, 32, (16), 1856-1862.

Novotny et al. Molybdenum intake influences molybdenum kinetics in men. J. Nutr. 137, 37-42 (2007).

O'Dowd et al., "Face Masks and Respirators in the Fight Against the COVID-19 Pandemic: A Review of Current Materials, Advances and Future Perspectives," Materials 2020, 13(15), 3363.

Olatunji, O.; et al. Microneedle-assisted transdermal delivery of acetylsalicylic acid (aspirin) from biopolymer films extracted from fish scales. Polymer Bulletin 2018, 75, (9), 4103-4115.

Omidinia-Anarkoli, A.; et al. An Injectable Hybrid Hydrogel with Oriented Short Fibers Induces Unidirectional Growth of Functional Nerve Cells. Small 2017, 13, (36).

O'Riordan K, Lee JC: *Staphylococcus aureus* capsular polysaccharides. Clin Microbiol Rev 2004, 17(1):218-234.

Padilla F, et al. Stimulation of bone repair with ultrasound: A review of the possible mechanic effects. Ultrasonics. 2014;54(5):1125-1145.

Panieri E, et al. ROS signaling and redox biology in endothelial cells. Cell Mol Life Sci. 2015, 72(17):3281-3303.

Pankey GA, et al. Clinical relevance of bacteriostatic versus bactericidal mechanisms of action in the treatment of Gram-positive bacterial infections. Clin Infect Dis. 2004;38(6):864-870.

Park, J.-H et al. Biodegradable polymer microneedles: fabrication, mechanics and transdermal drug delivery, Journal of controlled release 2005, 104, (1), 51-66.

Parlet CP, Kavanaugh JS, Crosby HA, Raja HA, El-Elimat T, Todd DA, Pearce CJ, Cech NB, Oberlies NH, Horswill AR: Apicidin Attenuates MRSA Virulence through Quorum-Sensing Inhibition and Enhanced Host Defense. Cell Rep 2019, 27(1):187-198 e186.

Patel et al., "Development of a Sonically Powered Biodegradable Nanogenerator for Bone Regeneration", 2019, University of Connecticut, 46 pages.

Pathak, R. K. et al. A nanoparticle cocktail: temporal release of predefined drug combinations. Journal of the American Chemical Society 2015, 137, (26), 8324-8327.

Patrick, J.; et al. A randomized trial to assess the pharmacodynamics and pharmacokinetics of a single dose of an extended-release aspirin formulation. Postgraduate medicine 2015, 127, (6), 573-580.

Paul, et al. Novel 3D analysis of Claudin-5 reveals significant endothelial heterogeneity among CNS microvessels. 86, 1-10 (2013).

Pavel A, et al. Prophylactic Antibiotics in Clean Orthopaedic Surgery. JBJS. 1974;56(4):777-782.

Pelletier, J.-P.; et al. In Efficacy and safety of oral NSAIDs and analgesics in the management of osteoarthritis: Evidence from real-life setting trials and surveys, Seminars in arthritis and rheumatism, 2016; Elsevier: pp S22-S27.

Peltoniemi et al. SR-PLLA and SRPGA miniscrews: Biodegradation and tissue reactions in the calvarium and dura mater. J. Craniomaxillofac. Surg. 27, 42-50 (1999).

Peng, X., et al. "A breathable, biodegiadable, antibacterial, and self-powered electronic skin based on all-nanofiber triboelectric nanogenerators." Science Advances 6.26 (2020): eaba9624.

Peterson RV, et al. The effect of frequency and power density on the ultrasonically-enhanced killing of biofilm-sequestered *Escherichia coli*. Colloids and Surfaces B: Biointerfaces. 2000;17(4):219-227.

Prausnitz, M. R. Engineering microneedle patches for vaccination and drug delivery to skin. Annual review of chemical and biomolecular engineering 2017, 8, 177-200.

Pressmeddelande, "Microneedle Drug Delivery Systems Market 2018 Segmentation, Demand, Growth, Trend, Opportunity and Forecast to 2023," My News Desk, <https://www.mynewsdesk.com/se/probe-way/pressreleases/microncedle-drug-delivery-systems-market-2018-segmentation-demand-growth-trend-opportunity-and-forecast-to-2023-2672909> dated Sep. 3, 2018.

Prokuski L. Prophylactic Antibiotics in Orthopaedic Surgery. JAAOS—Journal of the American Academy of Orthopaedic Surgeons. 2008; 16(5):283-293.

Qian, Y. et al. Performance of N95 Respirators: Filtration Efficiency for Airborne Microbial and Inert Particles. American Industrial Hygiene Association Journal 1998, 59 (2), 128-132.

Qiu, Y. et al. Enhancement of skin permeation of docetaxel: a novel approach combining microneedle and elastic liposomes. Journal of Controlled Release 2008, 129, (2), 144-150.

Queck SY, Jameson-Lee M, Villaruz AE, Bach TH, Khan BA, Sturdevant DE, Ricklefs SM, Li M, Otto M: RNAIII-independent target gene control by the agr quorum-sensing system: insight into the evolution of virulence regulation in *Staphylococcus aureus*. Mol Cell 2008, 32(1): 150-158.

Quinn, H. L. et al. Design of a dissolving microneedle platform for transdermal delivery of a fixed-dose combination of cardiovascular drugs. Journal of pharmaceutical sciences 2015,104, (10), 3490-3500.

(56) References Cited

OTHER PUBLICATIONS

Ratajska, M. et al. Studies on the Biodegradation of Chitosan in an Aqueous Medium. Fibres & Textiles in Eastern Europe 2003, (3 (42)), 75—79.

Raynor, P. C. et al. The Long-Term Performance of Electrically Charged Filters in a Ventilation System. Journal of occupational and environmental hygiene 2004, 1 (7), 463-471.

Resistance Who-TICGIoA: No time to wait: Securing the future from drug-resistant infections. In.; 2019. 28 pages.

Rigby KM, DeLeo FR: Neutrophils in innate host defense against *Staphylococcus aureus* infections. Semin Immunopathol 2012, 34(2):237-259.

Riggin, C. N.; et al. Intra-articular tibiofemoral injection of a nonsteroidal anti-inflammatory drug has no detrimental effects on joint mechanics in a rat model. Journal of Orthopaedic Research 2014, 32, (11), 1512-1519.

Ripolin, A; et al. Successful application of large microneedle patches by human volunteers. International journal of pharmaceutics 2017, 521, (1-2), 92-101.

Rizzello L, et al. Nanotechnology tools for antibacterial materials. Nanomedicine (Lond). 2013;8(5):807-821.

Roberts, M. S. et al. Percutaneous absorption of topically applied NSAIDS and other compounds: role of solute properties, skin physiology and delivery systems. Inflammopharmacology 1999,7,(4), 339.

Robertson JMC, et al. A comparison of the effectiveness of $TiO_2$ photocatalysis and UVA photolysis for the destruction of three pathogenic micro-organisms. Journal of Photochemistry and Photobiology A: Chemistry. 2005;175(1):51-56.

Rohrer, M. D. et al. Microwave Sterilization. Journal of the American Dental Association (1939) 1985, 110 (2), 194-198.

Roy S, et al. Disposable Patterned Electroceutical Dressing (PED-10) Is Safe for Treatment of Open Clinical Chronic Wounds. Advances in Wound Care. 2019;8(4):149-159.

Runyan CM, et al. Low-frequency ultrasound increases outer membrane permeability of Pseudomonas aeruginosa. The Journal of General and Applied Microbiology. 2006;52(5):295-301.

Ruparelia JP, et al. Strain specificity in antimicrobial activity of silver and copper nanoparticles. Acta Biomater. 2008;4(3):707-716.

Russell, R., Non-steroidal anti-inflammatory drugs and gastrointestinal damage—problems and solutions. Postgraduate medical journal 2001, 77, (904), 82-88.

Sadorsky, P., The Effect of Urbanization and Industrialization on Energy Use in Emerging Economies: Implications for Sustainable Development. American Journal of Economics and Sociology 2014, 73 (2), 392-409.

Salomoni R, et al. Antibacterial effect of silver nanoparticles in Pseudomonas aeruginosa. Nanotechnol Sci Appl. 2017;10:115-121.

Santora, M. et al. Covid Updates: Known Global Tool Reaches 200 Millions Virus Infections. Aug. 4, 2021. https://web.archive.org/web/20210804234532/https ://www.nytimes.com/live/2021/08/04/world/covid-delta-variant-vaccine (21 pages).

Schlesinger, E. et al. Poly caprolactone thin-film drug delivery systems: empirical and predictive models for device design. Materials Science and Engineering: C 2015, 57, 232-239.

Schlesinger, E.; et al. A tunable, biodegradable, thin-film polymer device as a long-acting implant delivering tenofovir alafenamide fumarate for HIV pre-exposure prophylaxis. Pharmaceutical research 2016, 33, (7), 1649-1656.

Schmook, F. P.; et al. Comparison of human skin or epidermis models with human and animal skin in in-vitro percutaneous absorption. International journal of pharmaceutics 2001, 215, (1-2), 51-56.

Schutze GE, Hall MA, Baker CJ, Edwards MS: Role of neutrophil receptors in opsonophagocytosis of coagulase-negative staphylococci. Infect Immun 1991, 59(8):2573-2578.

Sencadas et al., Local piezoelectric activity of single poly(L-lactic acid) (PLLA) microfibers. Appl. Phys. A 109,51-55 (2012).

Seth AK, et al. Noncontact, low-frequency ultrasound as an effective therapy against Pseudomonas aeruginosa—infected biofilm wounds. Wound Repair Regen. 2013;21(2):266-274.

Shah SR, et al. Evolving strategies for preventing biofilm on implantable materials. Materials Today. 2013;16(5):177-182.

Shah, S.; et al. Controversies and advances in non-steroidal anti-inflammatory drug (NSAID) analgesia in chronic pain management. Postgraduate medical journal 2012, 88, (1036), 73-78.

Shalumon KT, et al. Sodium alginate/poly(vinyl alcohol)/nano ZnO composite nanofibers for antibacterial wound dressings. Int J Biol Macromol. 2011;49(3):247-254.

Sheets, D.; et al. An Apparatus for Rapid and Nondestructive Comparison of Masks and Respirators. Review of Scientific Instruments 2020, 91 (11), 114101.

Shim, J.-H. et al. Efficacy of rhBMP-2 loaded PCL/PLGA/β-TCP guided bone regeneration membrane fabricated by 3D printing technology for reconstruction of calvaria defects in rabbit. Biomedical materials 9, 065006 (2014) (9 pages).

Shokri, J.; et al. Swellable elementary osmotic pump (SEOP): an effective device for delivery of poorly water-soluble drugs. European Journal of Pharmaceutics and Biopharmaceutics 2008, 68, (2), 289-297.

Shrivastava S, et al. Characterization of enhanced antibacterial effects of novel silver nanoparticles. Nanotechnology. 2007;18(22):225103 (9 pages).

Shuai et al., "Surface modification enhances interfacial bonding in PLLA/MgO bone scaffold," Materials Science and Engineering C, vol. 108, Mar. 2020, 110486.

Shuai, C. et al. nMgO-incorporated PLLA bone scaffolds: Enhanced crystallinity and neutralized acidic product. Materials & Designs 174, 107801 (2019).

Silva, E.; et al. Pdlla Honeycomb-Like Scaffolds with a High Loading of Superhydrophilic Graphene/Multi-Walled Carbon Nanotubes Promote Osteoblast in Vitro Functions and Guided in Vivo Bone Regeneration. Materials Science and Engineering: C 2017, 73, 31-39.

Sinatra, R. S.; el al. Efficacy and safety of single and repeated administration of 1 gram intravenous acetaminophen injection (paracetamol) for pain management after major orthopedic surgery. Anesthesiology: The Journal of the American Society of Anesthesiologists 2005, 102, (4), 822-831.

Smith et al. Direct observation of shear piezoelectricity in poly-L-lactic acid nanowires. APL Mater. 5, 074105 (2017) (8 pages).

Starr MB, et al. Coupling of piezoelectric effect with electrochemical processes. Nano Energy. 2015;14:296-311.

Stokes, A.; et al. The contribution of obesity to prescription opioid use in the United States. Pain 2019, 160, (10), 2255.

Subbiahdoss G, et al. Magnetic targeting of surface-modified superparamagnetic iron oxide nanoparticles yields antibacterial efficacy against biofilms of gentamicin-resistant staphylococci. Acta Biomater. 2012;8(6):2047-2055.

Sultana et al., Human skin interactive self-powered wearable piezoelectric bio-eskin by electrospun poly-L-lactic acid nanofibers for non-invasive physiological signal monitoring. J. Mater. Chem. B 5, 7352-7359 (2017).

Sutton et al., "Hospital-, Health Care-, and Community-Acquired MRSA: Estimates From California Hospitals, 2013," <https://www.hcup-us.ahrq.gov/reports/statbriefs/sb212-MRSA-Hospital-Stays-California-2013.jsp> dated Oct. 2016.

Szablowski, et al. Acoustically targeted chemogenetics for the non-invasive control of neural circuits. Nat. Biomed. Eng. 2, 475-484 (2018).

Taguchi, V. et al. Determination of drug stability in aspirin tablet formulations by high-pressure liquid chromatography. Journal of pharmaceutical sciences 1981, 70, (1), 64-67.

Tajitsu et al. Novel tweezers for biological cells using piezoelectric polylactic acid fibers. Ferroelectrics 320, 133-139 (2005).

Tajitsu, Y. Fundamental study on improvement of piezoelectricity of poly(1-ladic acid) and its application to film actuators. IEEE Trans. Ultrason. Ferroelectr. Freq. Control 60, 1625-1629 (2013).

(56) References Cited

OTHER PUBLICATIONS

Takeuchi, H.; et al. Influence of skin thickness on the in vitro permeabilities of drugs through Sprague-Dawley rat or Yucatan micropig skin. Biological and Pharmaceutical Bulletin 2012, 35, (2), 192-202.
Tams J, et al. Poly(l-lactide) bone plates and screws for internal fixation of mandibular swing osteotomies. Int J Oral Maxillofac Surg. 1996;25(1):20-24.
Tan, et al. Studies on Thermal Decomposition Mechanism and Kinetics of Aspirin [J]. Acta Physico-chimica Sinica 2004, Im 50-54. With English Abstract.
Tan, G., et al. "Surface-selective preferential production of reactive oxygen species on piezoelectric ceramics for bacterial killing." ACS applied materials & interfaces 8.37 (2016): 24306-24309.
Tao H, et al. Silk-based resorbable electronic devices for remotely controlled therapy and in vivo infection abatement. Proceedings of the National Academy of Sciences. 2014;111(49): 17385.
Tezel A, et al. Topical Delivery of Anti-sense Oligonucleotides Using Low-Frequency Sonophoresis. Pharm Res. 2004;21(12):2219-2225.
Thakur, R. R. S.; et al. Microneedle-mediated intrascleral delivery of in situ forming thermoresponsive implants for sustained ocular drug delivery. Journal of Pharmacy and Pharmacology 2014, 66, (4), 584-595.
Thammavongsa V, Kim HK, Missiakas D, Schneewind O: Staphylococcal manipulation of host immune responses. Nat Rev Microbiol 2015, 13(9):529-543.
Thermofisher Scientific. Residual Solvent Analysis Information. Jul. 14, 2019. https://web.archive.org/web/20190714025617/https://www.thermofisher.com/us/en/home/industrial/pharma-biopharma/pharma-biopharma-learning-center/pharmaceutical-qa-qc-information/residual-solvent-analysis-information.html (6 pages).
Timin, A. S., et al. "Multifunctional scaffolds with improved antimicrobial properties and osteogenicity based on piezoelectric electrospun fibers decorated with bioactive composite microcapsules." ACS applied materials & interfaces 10.41 (2018): 34849-34868.
Tong SY, Davis JS, Eichenberger E, Holland TL, Fowler VG, Jr.: *Staphylococcus aureus* infections: epidemiology, pathophysiology, clinical manifestations, and management. Clin Microbiol Rev 2015, 28(3):603-661.
Tran, K. T.; et al. Lithography-based methods to manufacture biomalerials at small scales. Journal of Science: Advanced Materials and Devices 2017, 2, (1), 1-14.
Tucho, G. T.; et al., Universal Use of Face Masks and Related Challenges During Covid-19 in Developing Countries. Risk Management and Healthcare Policy 2021, 14, 511.
Ueki, H.; et al. Effectiveness of Face Masks in Preventing Airborne Transmission of Sars-Cov-2. MSphere 2020, 5 (5), e00637-20.
Ummadi, S.; et al. Overview on controlled release dosage from. System 2013, 7, (8), 51-60.
Valentini, R. F., et al. Electrically charged polymeric substrates enhance nerve fibre outgrowth in vitro. Biomaterials 13, 183-190 (1992).
Van Acker H, et al. The Role of Reactive Oxygen Species in Antibiotic-Mediated Killing of Bacteria. Trends in Microbiology. 2017;25(6):456-466.
Varrone JJ, et al. Passive immunization with anti-glucosaminidase monoclonal antibodies protects mice from implant-associated osteomyelitis by mediating opsonophagocytosis of *Staphylococcus aureus* megaclusters. J Orthop Res 2014, 32(10):1389-1396.
Varrone JJ, Li D. Daiss JL, Schwarz EM: Anti-Glucosaminidase Monoclonal Antibodies as a Passive Immunization for Methicillin-Resistant *Staphylococcus aureus* (MRSA) Orthopaedic Infections. Bonekey Osteovision 2011, 8:187-194.
Vykhodtseva, et al. Progress and problems in tire application of focused ultrasound for blood-brain barrier disruption. Ultrasonics 48,279-296 (2008).
Vysakh et al., "A Comparative Analysis of Community Acquired and Hospital Acquired Methicillin Resistant *Staphylococcus Aureus*," J Clin Diagn Res. Jul. 2013; 7(7): 1339-1342.
Walmsley, A. et al. Ultrasound in dentistry. Part 2—periodontology and endodontics. J. Dent. 20, 11-17 (1992).
Walsh C. Molecular mechanisms that confer antibacterial drug resistance. Nature. 2000;406(6797):775-781.
Wang F, Gao W, Thamphiwatana S, Luk BT, Angsantikul P, Zhang Q, Hu CM, Fang RH, Copp JA, Pornpattananangkul D et al: Hydrogel Retaining Toxin-Absorbing Nanosponges for Local Treatment of Methicillin-Resistant *Staphylococcus aureus* Infection. Adv Mater 2015, 27(22):3437-3443.
Wang Y, et al. Piezo-catalysis for nondestructive tooth whitening. Nature Communications. 2020; 11(1): 1328.
Wang, C. et al. Enhanced cancer immunotherapy by microneedle patch-assisted delivery of anti-PD1 antibody. Nano letters 2016, 16, (4), 2334-2340.
Wang, C. et al. Silk Nanofibers as High Efficient and Lightweight Air Filter. Nano Research 2016, 9 (9), 2590-2597.
Wang, N. et al. Tunable Fabrication of Three-Dimensional Polyamide-66 Nano-Fiber/Nets for High Efficiency Fine Particulate Filtration. Journal of Materials Chemistry 2012, 22 (4), 1445-1452.
Wang, P. et al. Ultrasmall Barium Titanate Nanoparticles for Highly Efficient Hypoxic Tumor Therapy Via Ultrasound Triggered Piezocatalysis and Water Splitting. ACS nano 2021,11326-11340.
Wang, S. et al. Controlled release of levonorgestrel from biodegradable poly (D, L-lactide-co-glycolide) microspheres: in vitro and in vivo studies. International journal of pharmaceutics 2005, 301, (1-2), 217-225.
Wang, S. et al. Electret Polyvinylidene Fluoride Nanofibers Hybridized by Polytetrafluoroethylene Nanoparticles for High-Efficiency Air Filtration. ACS applied materials & interfaces 2016, 8 (36), 23985-23994.
Wang, Z. et al. Porous Bead-on-String Poly (Lactic Acid) Fibrous Membranes for Air Filtration. Journal of colloid and interface science 2015, 441, 121-129.
Wang, Z.-F. et al. Aspirin-triggered Lipoxin A4 attenuates mechanical allodynia in association with inhibiting spinal JAK2/STAT3 singaling in neuropathic pain in rats. Neuroscience 2014, 273, 65-78.
Ward AR, et al. Comparison of Heating of Nonliving Soft Tissue produced by 45 kHz and 1 MHz Frequency Ultrasound Machines. J Orthop Sports Phys Thcr. 1996;23(4):258-266.
Wartzek, et al. Triboelectricity in capacitive biopotential measurements. IEEE Trans. Biomed. Eng. 58, 1268-1277 (2011).
Who, "New report calls for urgent action to avert antimicrobial resistance crisis," <https://www.who.int/news/item/29-04-2019-new-report-calls-for-urgent-action-to-avert-antimicrobial-resistance-crisis> dated Apr. 29, 2019.
Who, Coronavirus Disease (Covid-19) Advice for the Public: When and How to Use Masks. https://www.who.int/emergencies/diseases/novel-coronavirus-2019/advice-for-public/when-andhow-to-use-masks (Updated Dec. 2021) (12 pages).
Who, Shortage of Personal Protective Equipment Endangering Health Workers Worldwide. https://www.who.int/news/item/03-03-2020-shortage-of-personal-protective-equipment-endangering-health-workers-worldwide. Mar. 3, 2020 (3 pages).
Wiese, A. D.; et al. Opioid analgesics and the risk of serious infections among patients with rheumatoid arthritis: a self-controlled case series study. Arthritis & rheumatology 2016, 68, (2), 323-331.
Witzleb et al. Exposure to chromium, cobalt and molybdenum from metal-on-metal total hip replacement and hip resurfacing arthroplasty. Acta Orthop. 77, 697-705 (2006).
Woltjer et al. (2016) "Optimization of piezo-MEMS layout for a bladder monitor" in 2016 IEEE International Ultrasonics Symposium (IUS) (IEEE, 2016), pp. 1-4.
Wu, S. et al. Surface Modification of Pure Magnesium Mesh for Guided Bone Regeneration: In Vivo Evaluation of Rat Calvarial Defect. Materials 12, 2684 (2019).
Wynn, R. F. et al. A small proportion of mesenchymal stem cells strongjy expresses functionally active CXCR4 receptor capable of promoting migration to bone marrow. Blood 104, 2643-2645 (2004).

(56) References Cited

OTHER PUBLICATIONS

Xin et al., A Site-Specific Integrated Col2. 3GFP Reporter Identifies Osteoblasts Within Mineralized Tissue Formed In Vivo by Human Embryonic Stem Cells. Stem cells translational medicine 3, 1125-1137 (2014).

Xiong, Z.-C et al. Flexible Hydroxyapatite Ultralong Nanowire-Based Paper for Highly Efficient and Multifunctional Air Filtration. Journal of Materials Chemistry A 2017, 5 (33), 17482-17491.

Xu X, et al. Strong vibration-catalysis of ZnO nanorods for dye wastewater decolorization via piezo-electro-chemical coupling. Chemosphere. 2018;193:1143-1148.

Xu, E. G.; et al.Preventing Masks from Becoming the Next Plastic Problem. Frontiers of environmental science & engineering 2021, 15 (6), 125.

Yang, M.; et al. Is Pm1 Similar to Pm2. 5? A New Insight into the Association of Pm1 and Pm2. 5 with Children's Lung Function. Environment International 2020, 145, 106092.

Yoshimoto, I et al. Development of layered PLGA membranes for periodontal tissue regeneration. Dent. Mater. 34, 538-550, (2018).

You H., et al. Strong piezo-electrochemical effect of multiferroic BiFeO3 square micro-sheets for mechanocatalysis. Electrochem Commun. 2017;79:55-58.

Yu, J.; et al. Glucose-responsive insulin patch for the regulation of blood glucose in mice and minipgs. Nature Biomedical Engineering 2020, 1-8.

Yu, Y. et al. Multifunctions of dual Zn/Mg ion co-implanted titanium on osteogenesis, angiogenesis and bacteria inhibition for dental implants. Acta Biomater. 49, 590-603 (2017).

Zhang, H. et al. Drug delivery systems for differential release in combination therapy. Expert opinion on drug delivery 2011, 8, (2), 171-190.

Zhang, J. et al. Biodegradable Electrospun Poly (Lactic Acid) Nanofibers for Effective Pm 2.5 Removal. Macromolecular Materials and Engineering 2019, 304 (10), 1900259.

Zhang, Q.; et al. Transboundary Health Impacts of Transported Global Air Pollution and International Trade. Nature 2017,543 (7647), 705-709.

Zhang, R. et al. Nanofiber Air Filters with High-Temperatuie Stability for Efficient Pm2. 5 Removal from the Pollution Sources. Nano letters 2016, 16 (6), 3642-3649.

Zhang, S.; et al. Spider-Web-Inspired PmO. 3 Filters Based on Self-Sustained Electrostatic Nanostiuctured Networks. Advanced Materials 2020, 32 (29), 2002361.

Zhang, Y. et al. Preparation of Nanofibrous Metal—Organic Framework Filters for Efficient Air Pollution Control. Journal of the American Chemical Society 2016, 138 (18), 5785-5788.

Zhao et al., Electrospun poly(L-lactic acid) nanofibeis for nanogenerator and diagnostic sensor applications. Macromol. Mater. Eng. 302, 1600476 (2017).

Zhou Y, Niu C, Ma B, Xue X, Li Z, Chen Z, Li F, Zhou S, Luo X, Hou Z: Inhibiting PSMalpha-induced neutrophil necroptosis protects mice with MRSA pneumonia by blocking the agr system. Cell Death Dis 2018, 9(3):362.

Zhu X, et al. Nanomedicine in the management of microbial infection—Overview and perspectives. Nano Today. 2014;9(4):478-498.

* cited by examiner

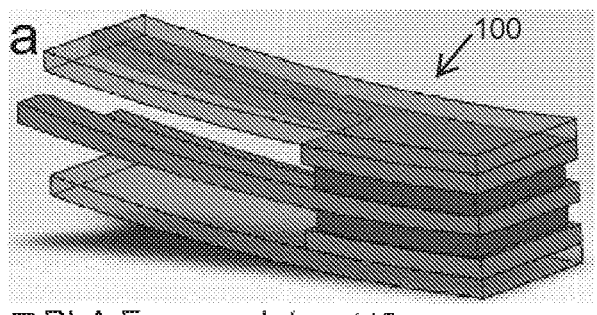
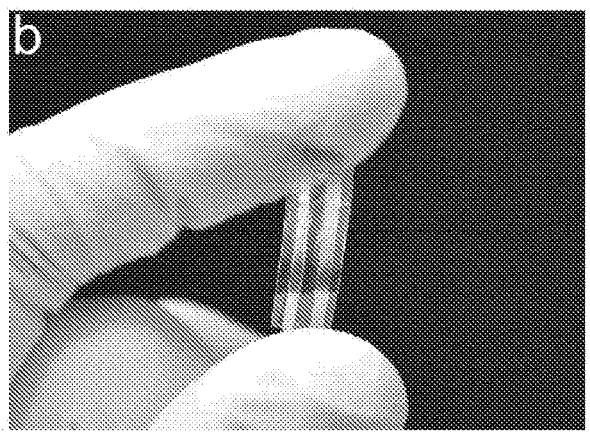
FIG. 4A  FIG. 4B
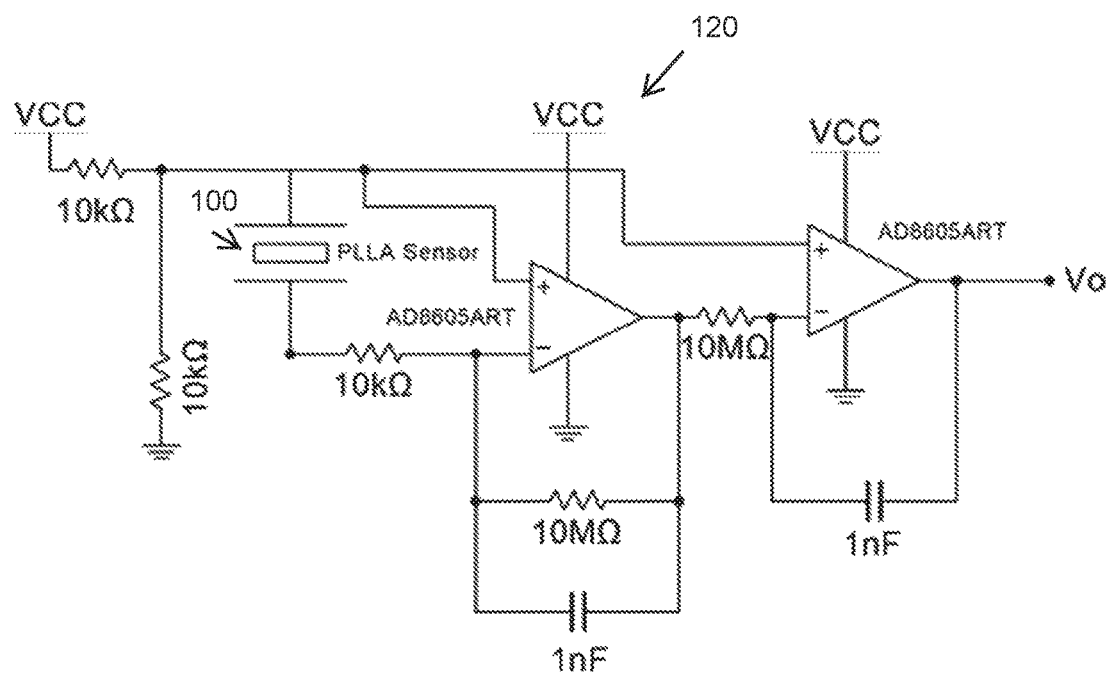
FIG. 4C

BIODEGRADABLE PRESSURE SENSOR

CROSS-REFERENCE TO RELATED APPLICATIONS

This application is the national stage filing under 35 U.S.C. § 371 of International Patent Application No. PCT/US2018/022441, filed Mar. 14, 2018 which is a non-provisional of and claims the benefit of U.S. Provisional Patent Application No. 62/470,968, filed on Mar. 14, 2017, and U.S. Provisional Patent Application No. 62/471,146, filed on Mar. 14, 2017. The contents of the entire contents of each of which are hereby incorporated by reference.

BACKGROUND OF THE INVENTION

Measuring vital physiological pressures is important for monitoring health status, preventing the buildup of dangerous internal forces in impaired organs, and enabling novel approaches of using mechanical stimulation for tissue regeneration. Pressure sensors are often required to be implanted and directly integrated with native soft biological systems. Therefore, the devices should be flexible and at the same time biodegradable to avoid invasive removal surgery that can damage directly interfaced tissues. Despite recent achievements in degradable electronic devices, there is still a tremendous need to develop a force sensor which only relies on safe medical materials and requires no complex fabrication process to provide accurate information on important biophysiological forces.

Existing biodegradable devices usually contain exotic and potentially toxic materials. When biodegradable devices degrade various by-products are produced. The by-products produced by existing biodegradable devices have not been confirmed for safety inside a human body. For example, a degradable brain pressure sensor (an intracranial pressure (ICP) sensor) has been developed that includes a fabricated n-doped silicon (Si) membrane and a fabricated p-doped Si membrane. The fabricated n-doped Si membrane and a fabricated p-doped Si membrane are bonded together to form a piezo-resistive pressure probe. The Si probe is encapsulated by a layer of silicon dioxide ($SiO_2$) along with a biodegradable polymer of polylactic glycolic acid (PLEA). While the brain pressure sensor has been shown to be degradable, future applications of the degradable brain pressure sensor in clinics and a human body are still questionable due to the use of exotic and potentially toxic materials, such as doped Si and $SiO_2$ (a main component of glass). Additionally, these materials are almost non-degradable over a short-term period of time. Furthermore, by-products from the degradation of these materials have not been tested for safety inside a human body.

SUMMARY OF THE INVENTION

Embodiments described herein relate to biodegradable piezoelectric devices, such as a biodegradable biomechanical sensor and a bioenergy-harvester. The biodegradable piezoelectric devices described herein contain only medical materials commonly used in U.S. Food and Drug Administration (FDA) approved medical implants, thereby offering a superior biocompatibility. By using solely erodible medical materials (for example, materials used in surgical sutures, vascular stents, drug carriers, and the like), the biodegradable piezoelectric device offers a great biocompatibility to a human body for implantation, which, as noted above, cannot be achieved by existing biodegradable devices. Currently, there are no biodegradable self-powering energy harvesters that can, for example, be used to power other erodible implant devices, electrical stimulation devices, or a combination thereof The biodegradable piezoelectric device described herein is based on a new piezoelectric processing of poly-L-lactic acid (PLLA). PLLA is a medical biopolymer that is used extensively for erodible surgical sutures, drug carriers, tissue scaffolds, and the like. In application, the biodegradable piezoelectric device may be configured to sense various biological pressures, including intracranial pressure (for example, in monitoring patients after brain traumatic injuries), cartilage joint force (for example, in monitoring forces exerted on osteoarthritis patients), intraocular pressure (for example, in the monitoring of aqueous humor pressure in glaucoma patients), intraabdominal pressure (for example, in the monitoring of abdominal organ pressure) or a combination thereof. Alternatively, or in addition, the biodegradable piezoelectric device may be configured to generate electricity from deformation of a diaphragm, lung, or heart or through external stimuli such as ultrasound. The generated electricity may be used to, for example, stimulate tissue regeneration, power other biomedical implants, and the like. Accordingly, the biodegradable piezoelectric device described herein may include a piezoelectric energy harvester that is biodegradable and safely used inside the human body.

In one example, the pressure sensor can precisely measure pressures in a wide range of 0-18 kPa and sustain a reliable performance for a period of 4 days in an aqueous environment. The PLLA piezoelectric sensor can be implanted inside the abdominal cavity of a mouse to monitor the pressure of diaphragmatic contraction. This piezoelectric sensor offers an appealing alternative to present biodegradable electronic devices for the monitoring of internal pressures. The sensor can be integrated with tissues and organs, forming self-sensing bionic systems to enable many exciting applications in regenerative medicine, drug delivery, and medical devices.

In one embodiment, the invention provides a biodegradable system comprising one or more magnesium wires encapsulated by poly-lactic acid and a biodegradable piezoelectric device connected to the one or more magnesium wires. The biodegradable piezoelectric device includes a first magnesium electrode, a second magnesium electrode, and a polymer film positioned between the first magnesium electrode and the second magnesium electrode, wherein the biodegradable piezoelectric device is encapsulated by a biodegradable polymer.

In another embodiment, the invention provides a biodegradable system comprising one or more molybdenum wires encapsulated by poly-lactic acid and a biodegradable piezoelectric device connected to the one or more molybdenum wires. The biodegradable piezoelectric device includes a first molybdenum electrode, a second molybdenum electrode, and a polymer film positioned between the first molybdenum electrode and the second molybdenum electrode, wherein the biodegradable piezoelectric device is encapsulated by a biodegradable polymer.

In yet another embodiment, the invention provides an implantable pressure sensor comprising a first layer of molybdenum, a second layer of a polymer film positioned on top of the first layer of molybdenum, a third layer of molybdenum positioned on top of the second layer of the polymer film, a fourth layer of a polymer film positioned on top of the third layer of molybdenum, a fifth layer of molybdenum positioned on top of the fourth layer of the polymer film, and an electrode extending from the first layer of molybdenum, the third layer of molybdenum, and the fifth layer of molybdenum, and a biodegradable polymer layer encapsulating the first layer, the second layer, the third layer, the fourth layer, and the fifth layer, and wherein the electrodes are connectable to an electronic circuit for measuring pressure exerted on the biodegradable polymer layer.

Other aspects of various embodiments will become apparent by consideration of the detailed description and accompanying drawings,

BRIEF DESCRIPTION OF THE DRAWINGS

FIG. 4A is a schematic of a biodegradable piezoelectric pressure-sensor according to another embodiment.

FIG. 4B is a picture of the biodegradable piezoelectric pressure-sensor of FIG. 4A.

FIG. 4C is a schematic circuit diagram of the biodegradable piezoelectric pressure-sensor of FIG. 4A connected to a charge amplifier.

DETAILED DESCRIPTION

Figure 1A:
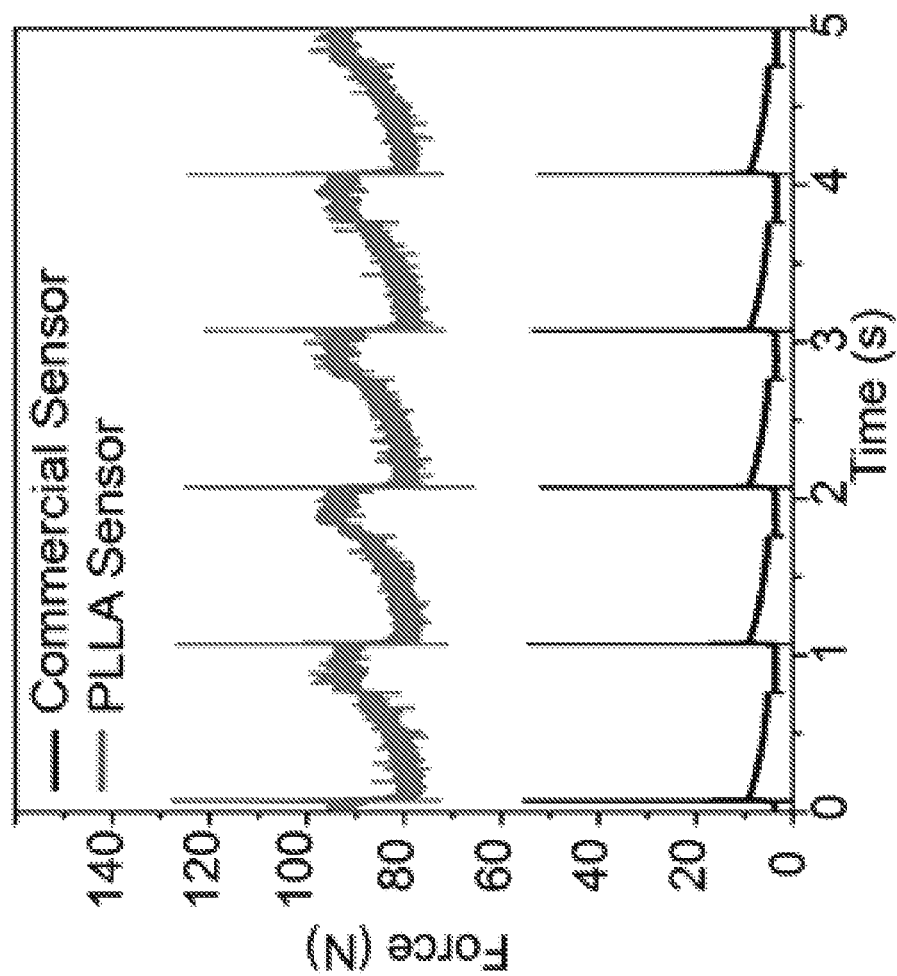
FIGS. 1A-1B illustrate the performance of a multi-layer poly-L-lactic acid (PLLA) piezoelectric device.

One or more embodiments are described and illustrated in the following description and accompanying drawings. These embodiments are not limited to the specific details provided herein and may be modified in various ways. Furthermore, other embodiments may exist that are not described herein. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way, but may also be configured in ways that are not listed. Furthermore, some embodiments described herein may include one or more electronic processors configured to perform the described functionality by executing instructions stored in non-transitory, computer-readable medium. Similarly, embodiments described herein may be implemented as non-transitory, computer-readable medium storing instructions executable by one or more electronic processors to perform the described functionality.

In addition, the phraseology and terminology used herein is for the purpose of description and should not be regarded as limiting. For example, the use of "including," "containing," "comprising," "having," and variations thereof herein is meant to encompass the items listed thereafter and equivalents thereof as well as additional items. The terms "connected" and "coupled" are used broadly and encompass both direct and indirect connecting and coupling. Further, "connected" and "coupled" are not restricted to physical or mechanical connections or couplings and can include electrical connections or couplings, whether direct or indirect. In addition, electronic communications and notifications may be performed using wired connections, wireless connections, or a combination thereof and may be transmitted directly or through one or more intermediary devices over various types of networks, communication channels, and connections. Moreover, relational terms such as first and second, top and bottom, and the like may be used herein solely to distinguish one entity or action from another entity or action without necessarily requiring or implying any actual such relationship or order between such entities or actions.

Piezoelectricity is a phenomenon which allows materials to convert deformation into electricity and vice versa. Piezoelectric materials are often used for force/pressure sensors, transducers, and generators. The materials can even be fabricated into nano- and microstructures and interfaced with soft tissues to monitor biological forces. Since piezoelectric materials can generate electricity from mechanical impact, they can serve as appealing sensing materials, alternative to the described passive semiconductors and capacitive polymers, for self-powered force sensors. However, commonly used piezoelectric materials such as lead zirconate titanate (PET) and polyvinylidene difluoride (PVDF) contain toxic or nonbiodegradable components, respectively, and thus are not favorable for implantation inside the human body. Poly-L-lactic acid (PLLA), a biodegradable polymer used extensively in FDA-approved implants, has recently been found to exhibit piezoelectricity when appropriately processed. The material exhibits shear piezoelectricity due to electrical polarity present in the carbon-oxygen double-bond branching off from the polymer backbone chain. Although possessing a modest piezoelectric response (5-15 pC/N), PLLA has a low dielectric constant, which allows the material to perform the same energy-conversion efficacy as the common piezoelectric polymer PVDF. By creating multilayers, one can achieve even higher piezoelectricity from PLLA, with an "effective" conversion efficiency, similar to that of ceramic PZT.

The biodegradable piezoelectric device (for example, a biodegradable piezoelectric sensor, actuator, or energy harvester) disclosed herein may be constructed from processed biocornpatible polymers, such as poly-lactic acid (PLA), poly-lactic glycolic acid (PLGA), and the like. A voltage created by the PLA layer may be collected on biodegradable, biocompatible magnesium (Mg) electrodes or molybdenum (Mo) electrodes.

In some embodiments, the biodegradable piezoelectric device includes a piezoelectric poly-L-lactic acid (PLLA) polymer. The piezoelectric PLLA polymer is positioned between Mg electrodes or Mo electrodes and encapsulated by one or more layers of high molecular weight (MW) PLA, The biodegradable piezoelectric device may be connected to Mg wires or Mo wires encapsulated inside PLA (Mg/PLA or Mo/PLA wires), which creates a biodegradable implanted system. As noted above, all of the biodegradable materials used for the biodegradable piezoelectric device and the implanted wires have been shown to be safe for use inside a human body. For example, Mg has been used for biodegradable vascular stents. Additionally, PLLA and PLA are common materials used for medical sutures and degradable bone screws. Through extensive studies, by-products from the degradation of these materials inside a human body have been proved to be biocompatible and are not known to cause harm.

A highly piezoelectric PLLA film has been developed for use in the biodegradable pressure sensor disclosed herein. In some embodiments, the biodegradable pressure sensor includes two PLLA layers along with inter-digital Mg electrodes, which creates a sensitive multi-layer pressure transducer. Specifically, the PLLA may be processed by mechanical-drawing techniques and thermal annealing to exhibit crystalline structures and piezoelectricity. In the thermal process, high MW PLLA may be solvent-casted on a Teflon substrate or heat-pressed to create a thin flat film. The film may then be heated and subjected to an annealing temperature of 90° C. for 1 hour. Next, piezoelectricity in the crystalline PLLA may be enhanced by uniaxially drawing the materials into a ratio of 6.5:1 at 90° C. for 7 hours. Alternatively, the piezoelectric film can be prepared by electrospinning a 4% w/v solution of PLLA dissolved in a 1:4 mixture of N,N-Dimethylformamide (DMF) and dichloromethane (DCM). The solution is pumped at a constant rate of 2 ml/hr through a 22 gauge needle with a 14 kV (kilovolts) applied to it. This electrified solution is then sprayed at a ground aluminum drum rotating at speeds from 500-4,500 rpm (rotations per minute). This results in a nanofiber mat of PLLA (diameter 300 nm) with varying degrees of alignment based on rotating drum speed. These fibrous mats are then annealed at 105° C. for 10 hr and allowed to cool to room temperature. They are then annealed at 160° C. for 10 hr and allowed to cool to room temperature. Finally, for both the stretched and electrospun films, the films need to be cut at a 45° angle relative to the oriented direction in order to harvest the shear piezoelectric signal of the film.

Figure 1B:
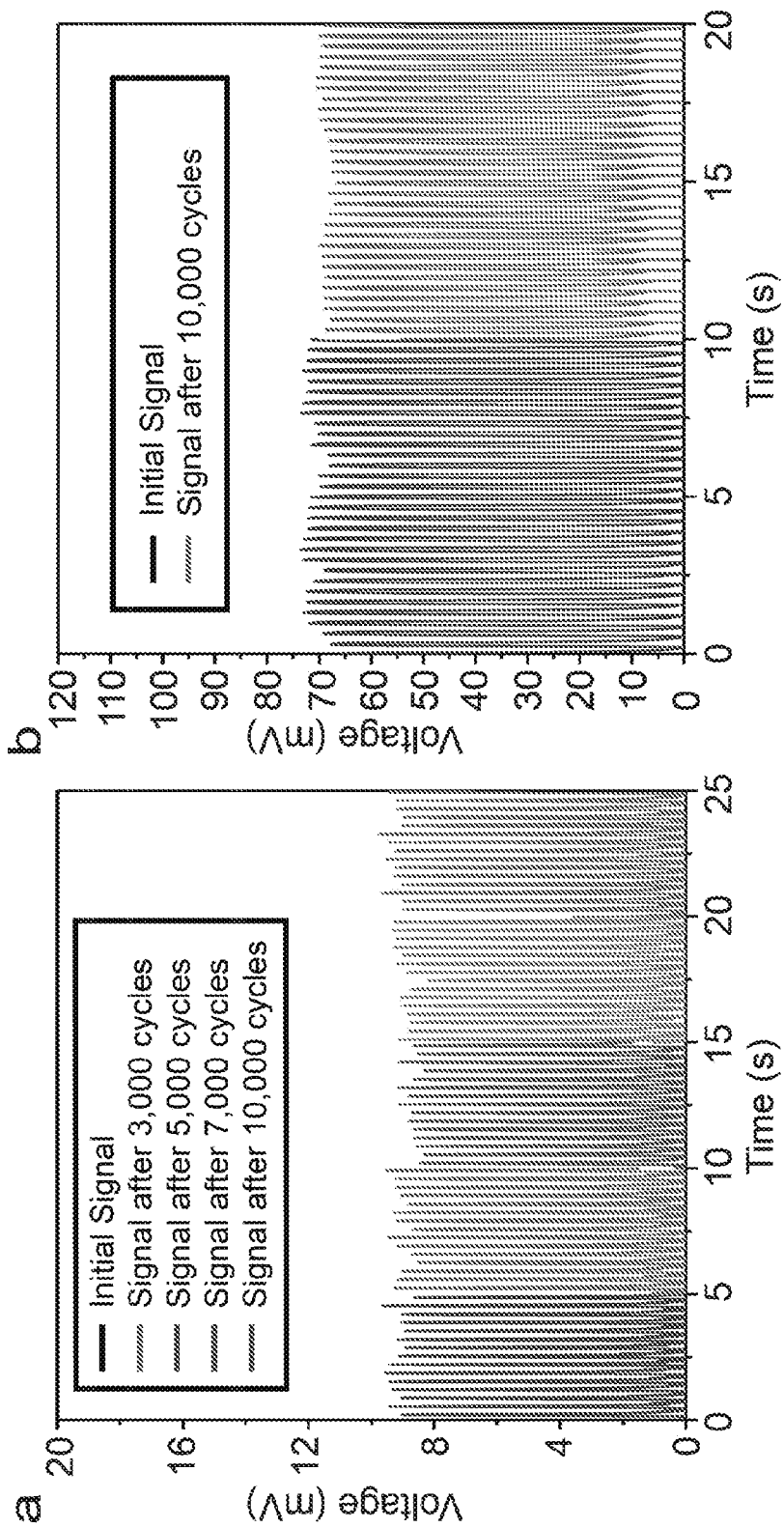

FIG. 1A illustrates the performance of a pressure sensor constructed as a multi-layer PLLA piezoelectric device in comparison to a commercially available piezoelectric sensor. As seen in FIG. 1A, when subjected to an impact force at a specified frequency, both the multilayer PLLA piezoelectric device and the commercially available piezoelectric sensor detect similar magnitudes of force. When under discrete impacting forces, as illustrated in FIG. 1B, the multi-layer PLLA piezoelectric device may output large amounts of charge. In particular, FIG. 1B illustrates the device generates the same signal over 10,000 cycles for both a 2 kPa (left panel) and 1 MPa (right panel). Therefore, the device can be used with a high degree of reliability in varying conditions of time and pressure.

Figure 2A:
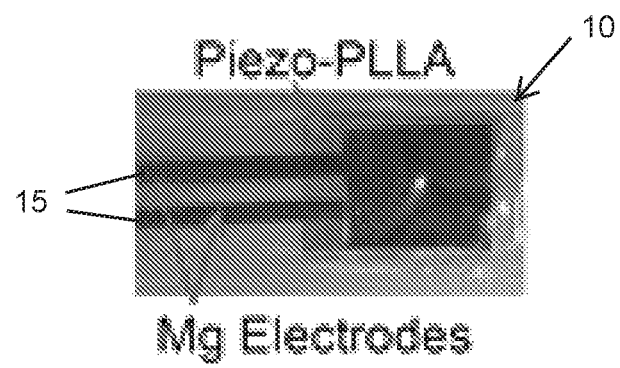
FIG. 2A is a picture of a biodegradable piezoelectric pressure-sensor.
Figure 2B:
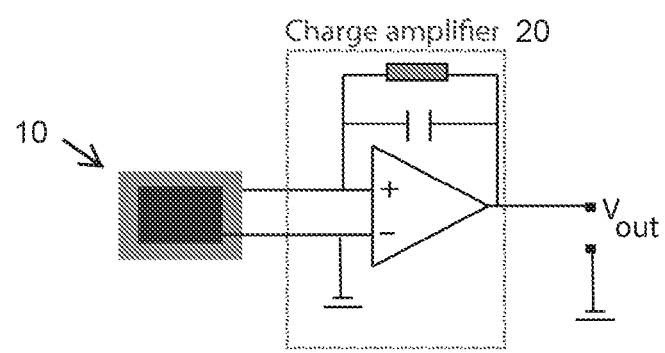
FIG. 2B is a schematic circuit diagram of a biodegradable piezoelectric pressure-sensor connected to a charge amplifier.

FIG. 2A illustrates a pressure sensor 10 according to an embodiment of the present invention. The pressure sensor 10 is constructed by depositing Mg on both sides of a PLLA film. The Mg may be deposited on both sides of the PLLA film using an e-beam evaporator. This configuration (Mg/PLLA/Mg) may then be encapsulated by layers of high MW PLA. In some embodiments, the pressure sensor 10 has a small size of ~1×1×0.03 cm (x, y, z) and a thickness of only ~300 μm. The encapsulating layer of PLA may be transparent and is not visible in FIG. 2A. The layers of the pressure sensor 10 may be stacked on each other. Electrodes 15 may be connected to create an additive polarization from all layers of the pressure sensor 10. The pressure sensor 10 may act as a pressure transducer to output charge from input pressure. Accordingly, in some embodiments, the pressure sensor 10 may be connected to a charge amplifier 20, as illustrated in FIG. 2B. By connecting the pressure sensor 10 to the charge amplifier 20, the charges generated by the pressure sensor 10 may be converted into voltage signals by the charge amplifier 20. The converted voltage signals may be displayed and processed by other electronics.

Figure 2C:
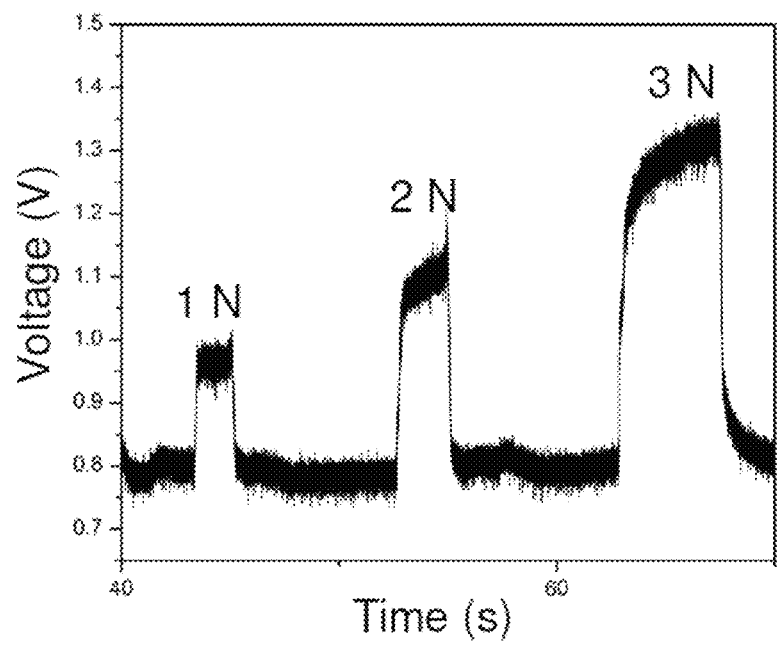
FIG. 2C illustrates output voltages of a biodegradable piezoelectric pressure-sensor in response to different applied pressures.
Figure 2D:
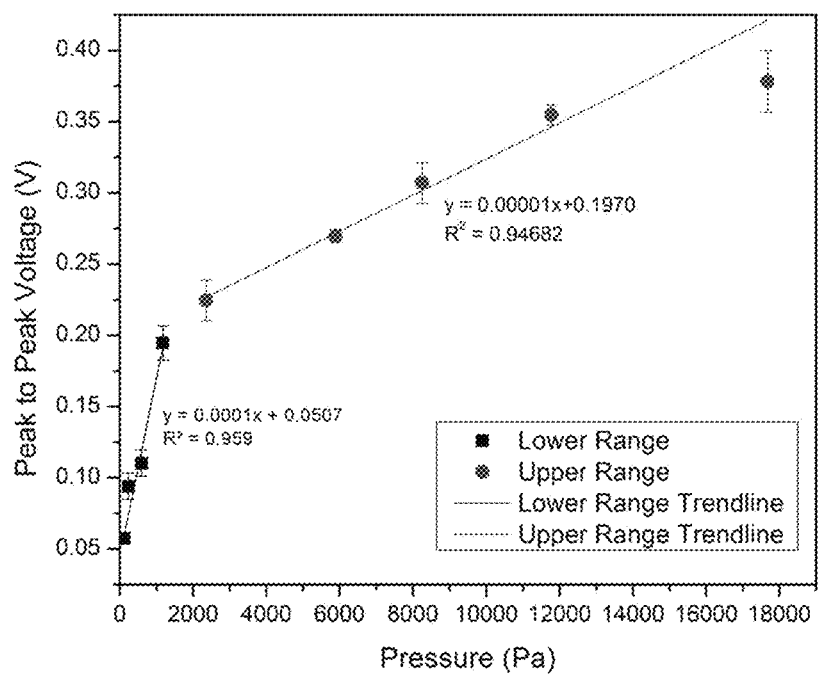
FIG. 2D illustrates pressures measurable by a biodegradable piezoelectric pressure-sensor.

FIG. 2C illustrates the response of the pressure sensor 10 to different applied forces and pressures (for example, 1N, 2N, and 3N). FIG. 2D illustrates a wide range of pressures that the pressure sensor 10 may measure. For example, the pressure sensor 10 may sense pressure within the range of 1-50 mmHg (in example, 0.1-6000 Pa), a typical range of ICP with a high sensitivity of ~13 mV/mmHg. Accordingly, the pressure sensor 10 described herein may be used to monitor pressure in both a normal range of 1-20 mmHg and an abnormal range of ~25-30 mmHg (for example, of an intracranial fluid in an injured brain). In other words, the pressure sensor 10 may monitor two different pressure ranges for two different linear fits, as illustrated in FIG. 2D.

Figure 3A:
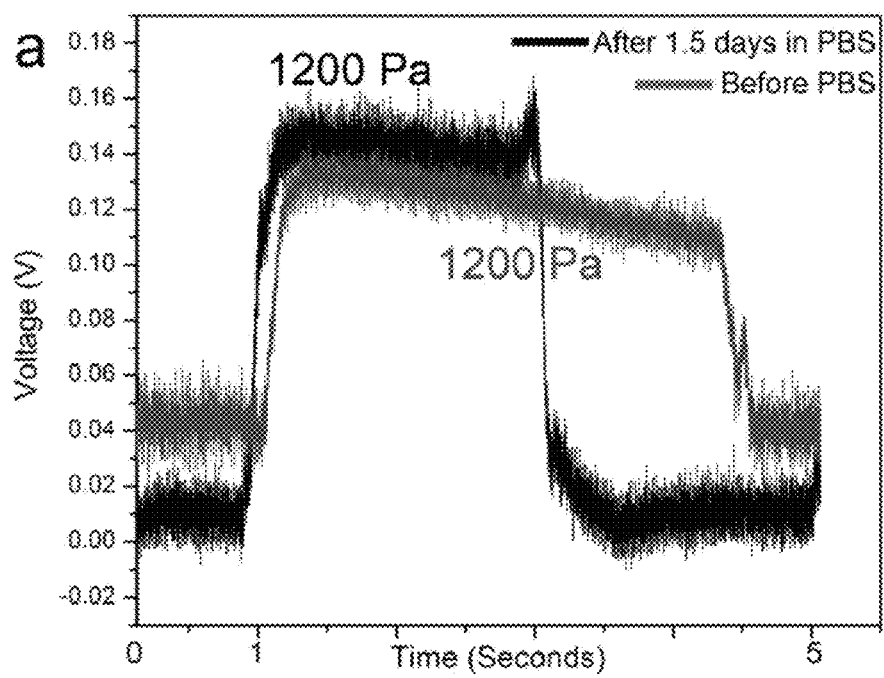
FIG. 3A illustrates a voltage response to an applied pressure for a biodegradable piezoelectric pressure-sensor before and after 1.5 days in vitro degradation.
Figure 3B:
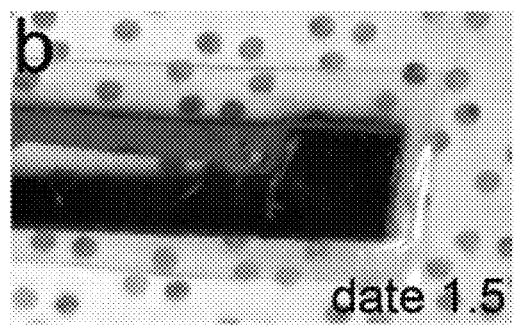
FIG. 3B illustrates a piezoelectric sensor submerged in an aqueous environment of saline solution PBS after 1.5 days.
Figure 3C:
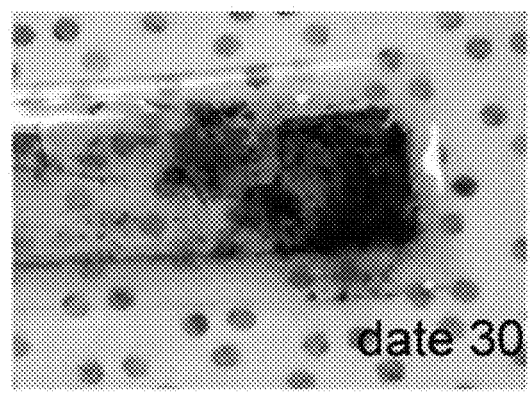
FIG. 3C illustrates a piezoelectric sensor submerged in an aqueous environment of saline solution PBS after 30 days.

By fabricating an encapsulating layer of PLA (MW 200 kD) with a thickness of 50 μm, the performance of the pressure sensor 10 may be sustained for 1.5 days. In other words, the pressure sensor 10 may respond to applied pressure after 1.5 days inside an aqueous environment of saline solution PBS. For example, as illustrated in FIG. 3, the pressure sensor 10 produces the same applied pressure after 1.5 days submerged inside the PBS solution. The functional lifetime of the pressure sensor 10 may be tuned by engineering the encapsulating PLA layers. For example, an increase in thickness or molecular weight will increase the functional lifetime of the pressure sensor 10. In other words, the functional lifetime of the pressure sensor 10 depends on the MW and thickness of the PLA. However, the pressure sensor 10 will eventually degrade leaving no harm to the body for implantation. For example, as illustrated in FIG. 3C, the pressure sensor 10 starts to degrade after 30 days submerged inside the PBS solution.

FIG. 4A illustrates a pressure sensor 100 according to another embodiment of the present invention. As shown in FIG. 4A, the sensor structure includes two layers of a polymer film (e.g., piezoelectric PLLA) 105, sandwiched between biodegradable metal (e.g., molybdenum (Mo)) electrodes 110 with an encapsulating biodegradable polymer layer (e.g., polylactic acid (PLA)) 115. It is noted that the sensor structure can include more or fewer layers than what is shown in the figures, For example, some constructions of the sensor 100 may utilize three layers of polymer film, such as piezoelectric PLLA 105 and four layers of a biodegradable metal, such as Mo, As another example, some constructions of the sensor 100 may utilize one layer of polymer film, such as piezoelectric PLLA 105 and two layers of a biodegradable metal, such as Mo. Additionally, the encapsulating layer 115 may include two or more layers 115 of biodegradable polymer.

The pressure sensor 100 may be constructed by depositing Mo on both sides of the polymer film using an e-beam evaporator. The polymer film layer 105 is sandwiched between the biodegradable metal layers 110 in a manner to prevent the biodegradable metal layers from making contact. The Mo electrodes 110 can also be cut out of Mo foil, allowing for easier sensor fabrication, This configuration (Mo/PLLA/Mo) may then be encapsulated by layers of high MW PLA 115. In sonic embodiments, the pressure sensor 100 has a small size of ~5×5×0.2 mm (x, y, z), thereby making the pressure sensor flexible (see FIG. 4B). Mo is used for implanted cardiovascular stents while PLA and PLLA are often used for bone screws and tissue scaffolds thereby making these materials suitable for this biodegradable sensor application. In some constructions, the thickness of the pressure sensor 100 can be reduced, making it even more flexible and facilitating device integration with soft tissues and organs to form a self-sensing bionic system. This can enable many applications in regenerative medicine, drug delivery, and medical devices.

The encapsulating layer of PLA 115 may be transparent as schematically shown in FIG. 4A. Although not fully shown in FIG. 4A, the encapsulating layer 115 fully surrounds the sensor 100 as shown in FIG. 4B. Layers of the pressure sensor 100 may be stacked on each other. The electrodes 110 may be connected to create an additive polarization from all layers of the pressure sensor 100. The pressure sensor 100 may act as a pressure transducer to output charge from input pressure. Accordingly, in some embodiments, the pressure sensor 100 may be connected to a charge amplifier 120, as illustrated in FIG. 4C. By connecting the pressure sensor 100 to the charge amplifier 120, the charges generated by the pressure sensor 100 may be converted into voltage signals by the charge amplifier 120. The converted voltage signals may be displayed and processed by other electronics.

Figure 4D:
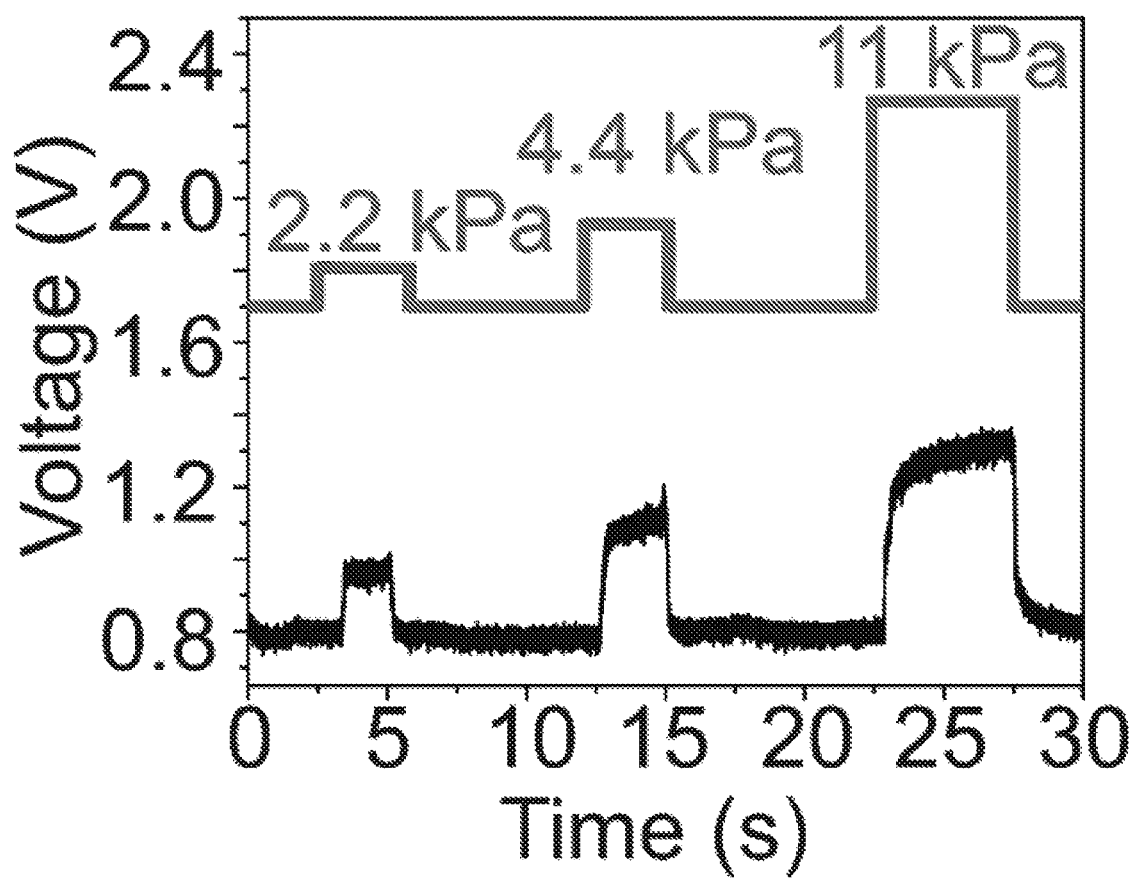
FIG. 4D illustrates output voltages of the biodegradable piezoelectric pressure-sensor of FIG. 4A in response to different applied pressures.
Figure 4E:
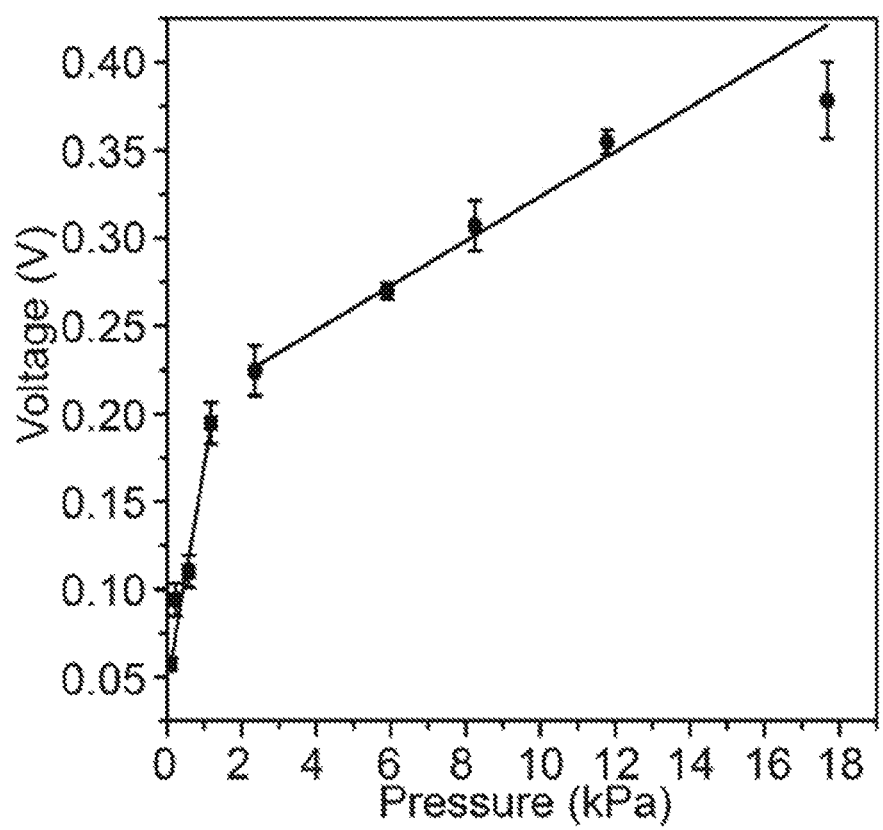
FIG. 4E illustrates a calibration curve for the biodegradable piezoelectric pressure-sensor of FIG. 4A.

FIG. 4D illustrates the response of the pressure sensor 100 to different applied forces and pressures (for example, 2,2 kPa, 4.4 kPa, and 11 kPa). FIG. 4E illustrates a wide range of pressures that the pressure sensor 100 may measure. For example, the pressure sensor 100 may sense pressure within the range of 1-50 mmHg (in example, 0.1-18,000 Pa), a typical range of ICP with a high sensitivity of ~13 mV/mmHg. Accordingly, the pressure sensor 100 described herein may be used to monitor pressure in both a normal range of 1-20 mmHg and an abnormal range of ~25-30 mmHg (for example, of an intracranial fluid in an injured brain). In other words, the pressure sensor 100 may monitor two—different pressure ranges for two different linear fits, as illustrated in FIG. 4E.

Figure 5A:
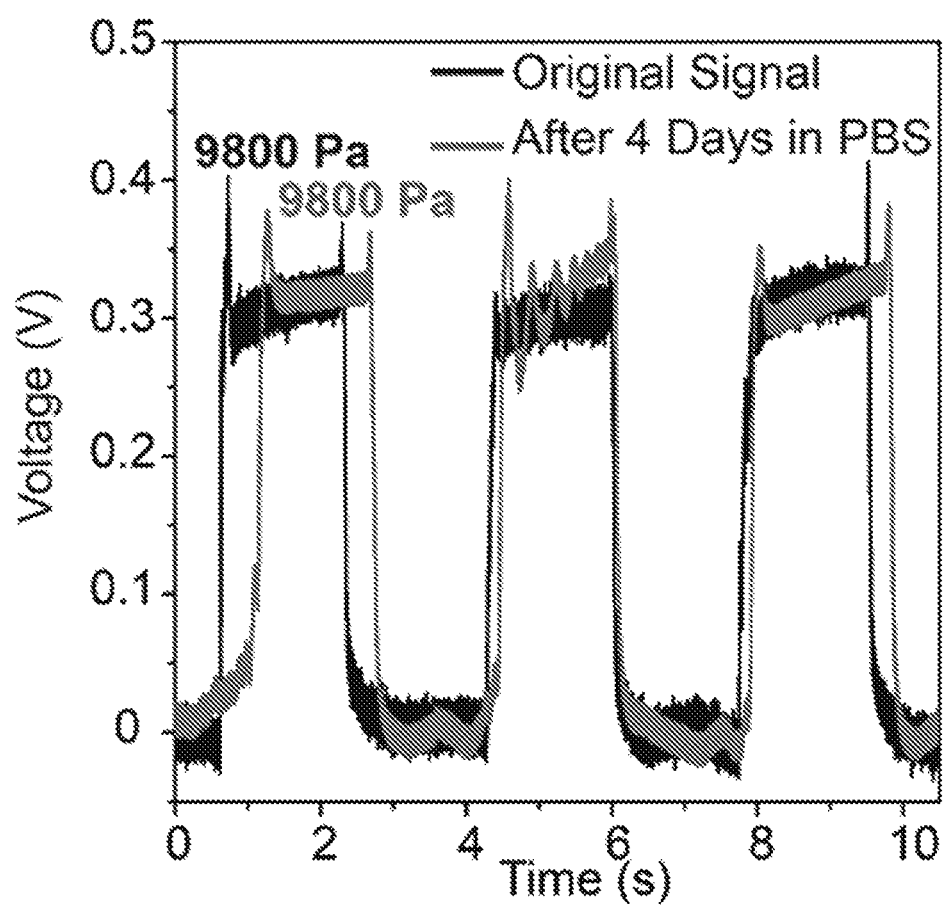
FIG. 5A illustrates a voltage response to an applied pressure for a biodegradable piezoelectric pressure-sensor before and after 4 days in vitro degradation.

By fabricating an encapsulating layer of PLA (MW 380 kD) with a thickness of 100 μm, the performance of the pressure sensor 100 may be sustained for 4 days. In other words, the pressure sensor 100 may respond to applied pressure after 4 days inside an aqueous environment of saline solution PBS heated to 37° C. For example, as illustrated in FIG. 5A, the pressure sensor 100 produces the same applied pressure after 4 days submerged inside the PBS solution. The functional lifetime of the pressure sensor 100 may be tuned by engineering the encapsulating PLA layers or through the use of additional biodegradable materials such as polycaprolactone (PCL), poly(glycerol sebacate) (PGS), poly (octamethylene maleate [anhydride] citrate) (POMaC) etc. For example, an increase in thickness or molecular weight will increase the functional lifetime of the pressure sensor 100. In other words, the functional lifetime of the pressure sensor 100 depends on the MW and thickness of the encapsulating material, in this case PLA. However, the pressure sensor 100 will eventually degrade leaving no harm to the body or surrounding tissues after implantation. For example, as comparatively illustrated in FIGS. 5B and 5C, the pressure sensor 100 starts to degrade after 56 days submerged inside the PBS solution.

In some embodiments, the pressure sensor 10, 100 includes an implant device with a battery for a short time period. In particular, the battery may be replaced by the pressure sensor, which may harvest deformation of organs, such as a heart or a lung, to generate electrical power. After a controllable desired time period, the pressure sensor will self-vanish and degrade away without any resulting harm to a human body. In some embodiments, the pressure sensor 10, 100 includes an implanted force sensor for measuring and monitoring important biological pressures, such as intracranial pressure, intra-cartilage pressure, intra-abdominal pressure, ocular pressure, and the like. In some embodiments, the pressure sensor 10, 100 includes an implanted electrical stimulator, such as a bone stimulator. The 10, 100 may self-harvest organ deformation and generate electrical stimulation. Accordingly, the pressure sensor 10, 100 avoids the need to perform an invasive removal surgery for such implanted devices, avoiding potential damage to surrounding tissues.

EXAMPLE

Figure 6:
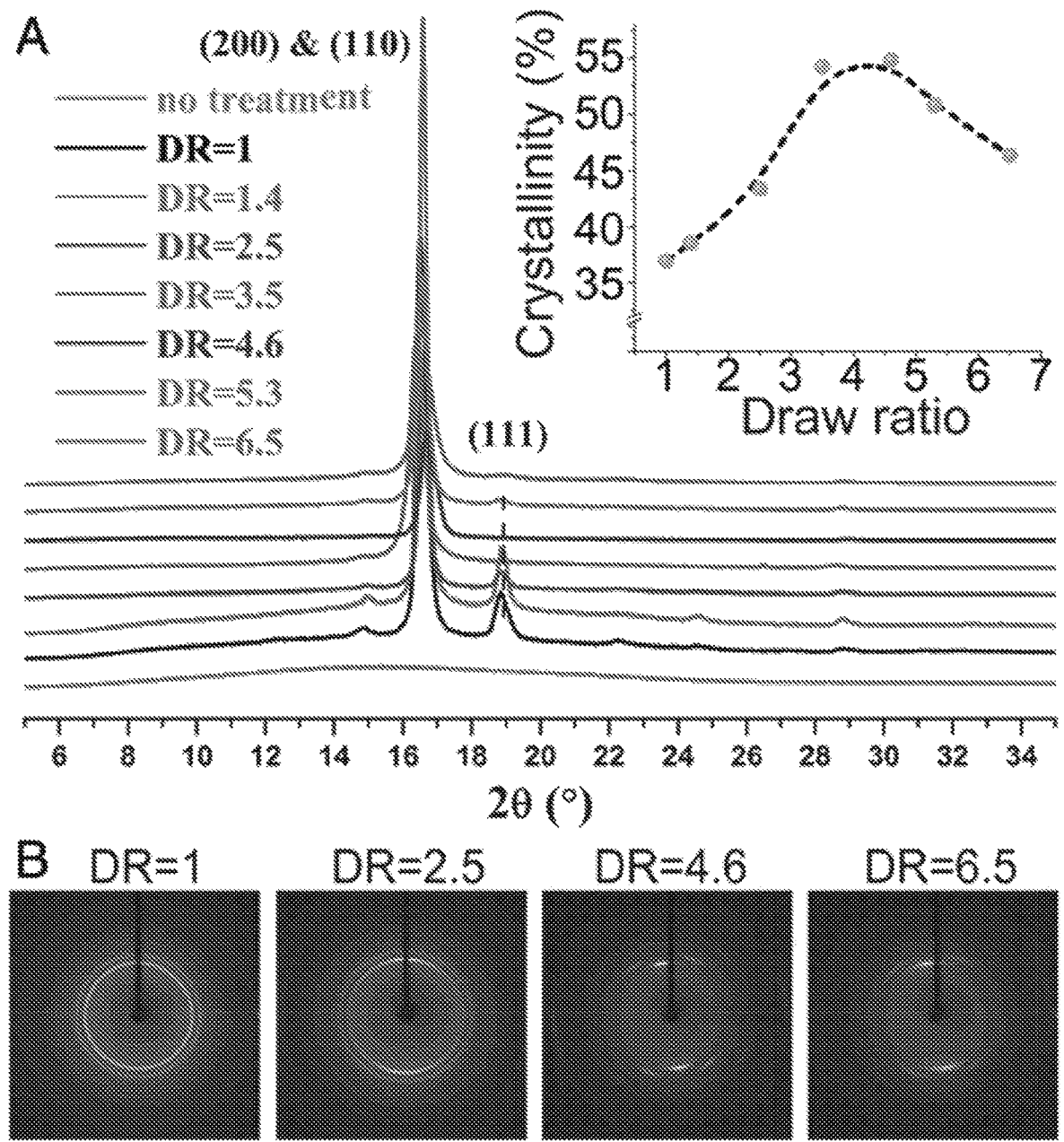
FIG. 6A illustrates a characterization of crystallinity and polymer chain orientation for processed PLLA and results from one-dimensional (1D) X-ray Diffraction (XRD) of stretched PLLA films with different draw ratios (DRs). The inset image illustrates crystallinity percentage of the processed PLLA for different DRs, quantified from the ID XRD spectrum.
FIG. 6B illustrates two-dimensional XRD images showing polymer chain's orientation of the stretched PLLA films with different DRs.

To make PLLA piezoelectric, the two major material properties that need to be improved are the crystallinity and orientation degree of the polymer chains. The net polarization, appearing in PLLA under applied force, is due to the relative alignment of the carbon—oxygen double bonds (C=O) branching out from the PLLA backbone. In normal conditions (without applied force), all polarizations from the C=O bonds along a PLLA polymeric chain are canceled out but shear stress will align and direct these polarizations more in one direction, generating a nonzero out-of-plane polarization in a single polymeric chain. To obtain a net polarization over a bulk PLLA film, these polymeric chains need to be oriented in the same direction from aligned crystalline domains. The mechanism of shear piezoelectricity for polymers with chiral structures has been well-described. The improvement of crystallinity and alignment is performed by thermal annealing and mechanical stretching processes, respectively. While PLLA can be transformed into a piezoelectric material through other processes like electrospinning, the inherently rough surface of a nanofiber film potentially causes unwanted triboelectric error and inconsistent readings in sensing applications. First, a thin PLLA film is created by heat compression. The film is then mechanically stretched at an annealing temperature of 90° C. The initial length of the PLLA film is then compared with the final stretched length to determine the draw ratio. FIG. 6A describes the one-dimensional X-ray diffraction (XRD) of stretched PLLA films with different draw ratios (DRs), The processed PLLA often exhibits three crystalline orientations of [111], [200], and [110], yet once the films reach a DR of 3.5, the (111) crystal face disappears and, at the same time, the intensity of the (200) and (110) peaks increases. This represents a change from the α-form crystal structure, which has a left-handed $10_3$ helical conformation, to the β-form crystal structure, which has a $3_1$ helical conformation. In other words, the crystalline domains are oriented or aligned more in the [200] and [110] directions under a large stretching force. Additionally, from the XRD data, the crystallinity degree for the PLLA films with different DRs could be quantified, based on the ratio of the area underneath the [200] and [110] peaks to the area underneath the entire curve, as seen in FIG. 6A (Inset). The data show the crystallinity percentage of the PLLA films increases with increasing DR up to ~5. Once a larger DR is employed, a clear downward trend is seen. Likewise, the stretching with larger DRs improves orientation degree of the crystal domains, as seen in the 2D XRD image of FIG. 6B, and provides the maximal alignment of crystal domains (quantified through Herman's orientation factor) at the DR ~5. These results explain an optimal DR (~5) to obtain the best piezoelectric effect, as previously reported.

To use the shear piezoelectricity in the PLLA to sense normal out-of-plane stress, the PLLA film needs to be further processed to translate the normal stress into in-plane shear, which is the driving force for piezoelectric outputs. By deriving a mechanical model based on the constitutive shear piezoelectric equations, a relationship between the out-of-plane normal stress and the in-plane shear as well as the resulting electrical field across the two major top and bottom surfaces of the PLLA film, upon applied normal stresses can be obtained. A theoretical derivation shows a linear relationship between voltage output and applied force, and that the PLLA film with a cutting angle of 45°, relative to the stretching direction, exhibits the maximal piezoelectric output in both impact and vibration modes. These theoretical analyses are also supported by experimental results. Therefore, the PLLA film was cut at an angle of 45°, relative to the stretching direction for all sensing devices developed later on. For convention, a "treated" PLLA is a film which has gone through an annealed stretching process and a 45° cutting, while a "processed" PLLA is a film which has only gone through annealed stretching.

Figure 7:
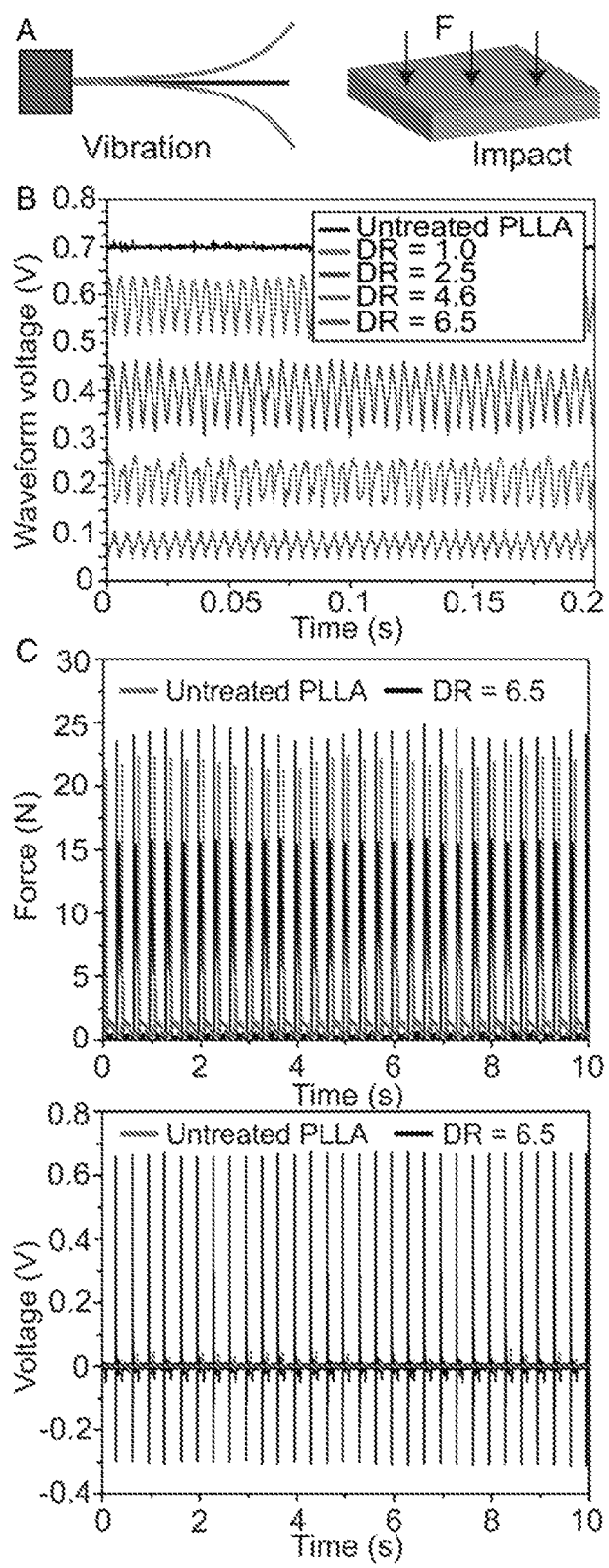
FIG. 7A illustrates a characterization of piezoelectric PLLA output from vibration and impact modes. The left image illustrates a simplified schematic representing the vibration, and the right image illustrates impact methods used to characterize the PLLA. F, denotes force.
FIG. 7B graphically illustrates voltage output from the treated PLLA with different DRs under a vibration at 200 Hz.
FIG. 7C illustrates voltage output from an untreated PLLA (red) and treated PLLA (black, DR=6.5) (Bottom graph) and under the same impact force (Top graph).

The piezoelectric outputs of the treated PLLA films under mechanical strains/forces through vibration and impact testing was assessed. Both procedures have been employed for the characterization of other piezoelectric materials. FIG. 7A provides simplified diagrams illustrating the two procedures utilized.

In the vibration system, a film made of the treated PLLA, sandwiched between aluminum foil electrodes and encapsulated in Kapton tape, was tightly affixed to the middle of the top portion of a polycarbonate beam with Kapton tape. Kapton tape was used to minimize any errors in signal measurement due to triboelectric effects. Note that nondegradable materials for electrodes and encapsulators were used to characterize piezoelectricity of PLLA with different draw ratios due to their easy fabrication, flexibility, and durability while functional-sensing devices described later were made of completely bioresorable materials. All of the sensors used in this experiment have the same area of 161.29 $mm^2$, with the thickness of each sample decreasing with increasing DR. The thicknesses of the PLLA samples used were 29, 68, 46, 27, and 20 um for the 0 (unstretched), 1, 2.5, 4.6, and 6.5 DR samples, respectively. One end of the beam is fixed and the other end of the beam is attached to an actuator which can be controlled to move at a desired frequency and amplitude. This resulted in the beam oscillating up and down, thus subjecting the PLLA sensor to mechanical strains (FIG. 7A, Left). In the impact system, the same actuator is affixed with a dynamic force sensor and driven by a defined voltage waveform to apply consistent normal forces on the PLLA sensor (FIG. 7A, Right). In both testing methods, the voltage output is measured by an oscilloscope. FIG. 7B illustrates open-circuit voltage outputs from PLLA. films of different DRs subjected to a 200-Hz vibration force that resulted in an elongation strain of about $6 \times 10^{-6}$ (measured by a strain gauge). The signal generated from the four treated PLLA samples of different DRs clearly shows piezoelectric waveform outputs with the same frequency as that of the mechanical input (200 Hz) while the untreated PLLA film (control sample) resulted in only noise. While the data show the sample with a DR of 2.5 has the largest signal output, it is not conclusive that this is an optimal DR. The sample thicknesses, due to mechanical stretching, are not precisely controlled, thus the mechanical properties and resonant frequencies of each film are expected to be different. FIG. 7C illustrates a typical open-circuit voltage output from the impact testing of a treated PLLA film with DR of ~6.5. An input force of ~23 N (about 1.4 kPa) resulted in a peak-to-peak voltage output of 0.9 V from the treated PLLA, while a non-treated PLLA. resulted in only noise. The piezoelectric outputs increased with increasing applied force in a linear manner.

Using reported mechanical properties of PLLA and the aforementioned model, a piezoelectric constant $d_{14}$ of ~11 pC/N can be estimated and a good fit between experimental data and theoretical calculations can be obtained for both the impact and vibration modes. The same modeling results, obtained from two independent experiments, and the consistency between experimental and theoretical calculations validate our mechanical model and reinforce the estimated $d_{14}$, which is also in the range of previous reports.

After confirming piezoelectricity in the treated PLLA, a biodegradable PLLA-based force sensor was fabricated. The biodegradable sensor was fabricated using a combination of the piezoelectric PLLA, molybdenum electrodes, and encapsulating PLA layers. The treated piezoelectric PLLA film has an area of 5×5 mm² and a thickness of 27 µm. The molybdenum electrodes are cut out of a sheet and affixed to the top and bottom of the PLLA film. Care was taken to ensure the electrodes were not shorted together. The PLLA/ Mo assembly was then sandwiched between sheets of PLA. If higher sensitivity was needed, more piezoelectric PLLA layers were added to fabricate a multilayer device. The PLA encapsulating layers were initially sealed together using a biodegradable PLLA glue. The PLA encapsulator was then thermally sealed by using a commercial plastic sealer at a temperature of ~200° C. for 4 s.

After the fabrication process, the sensitivity of this biodegradable piezoelectric PLLA sensor was assessed. The relatively low and bipolar output voltage (i.e., including negative and positive peaks) of PLLA was not ideal for use to visualize force response. Therefore, a charge amplifier circuit was built to convert the force-induced charge into an easy-to-visualize voltage signal. By placing different predefined weights on the sensor, different known forces/pressures are applied on the device to calibrate the voltage output. As can be seen from FIG. 4D, there were clearly distinguishable peaks for different magnitudes of input forces. Additionally, under the same applied pressure, the sensor generated a defined and consistent voltage pulse. The clear and distinguishable signals allowed us to construct a calibration curve (FIG. 4E). This calibration curve could be divided into two linear regions which are usable for measuring pressures in the wide range of 0-18 kPa. This pressure range is relevant to many important biophysiological pressures. Examples include intracranial pressure (from 0 to 2.7 kPa), intraocular pressure (from 0 to 5.3 kPa), etc.

The accuracy of the sensor was evaluated by comparing the device's reading with a commercially available piezoelectric quartz force sensor (208C02; PCB Piezotronics). To do this, the sensor was first calibrated as previously described. Next the PLLA sensor was affixed to a beam and covered with an aluminum plate in the impact-testing device, taking great care to prevent triboelectric signal error by sandwiching the sensor in between sheets of PLA. Using the calibration curve developed for this sensor, the voltage output from the charge amplifier circuit was then converted to a force value. As can be seen in FIG. 1A, the resulting signal closely represents the magnitude of impact force measured by the commercial sensor. The only major difference in signals is the inverted nature of our sensor, which is due to the inverting nature of the charge amplifier circuit. The accuracy of the sensor was also confirmed under 10,000 cycles of a 2-kPa and 1-MPa force, ensuring reliability for long-term measurements.

After verifying the accuracy of the sensor, the next goal was to show its viability during degradation. As the biodegradable nature of the PLA, Mo, and PLLA would suggest, it was important to show that the sensor can physically degrade. However, the sensor should maintain its ability to measure force during some portion of its degradation lifespan for use in various applications in vivo. The sensor was placed in PBS at the physiological temperature 37° C. and the device was recalibrated every 24 h. FIG. 5A illustrates the sensor's typical output signals before and after 4 days of degradation. Under the same applied pressure (9.8 kPa), the magnitude of the sensor's signal output was still the same after 4 days. This result was also confirmed in vivo by implanting the sensor into the backs of mice for a period of 2, 4, 8, and 16 days.

Figures 5B, 5C, 5D:
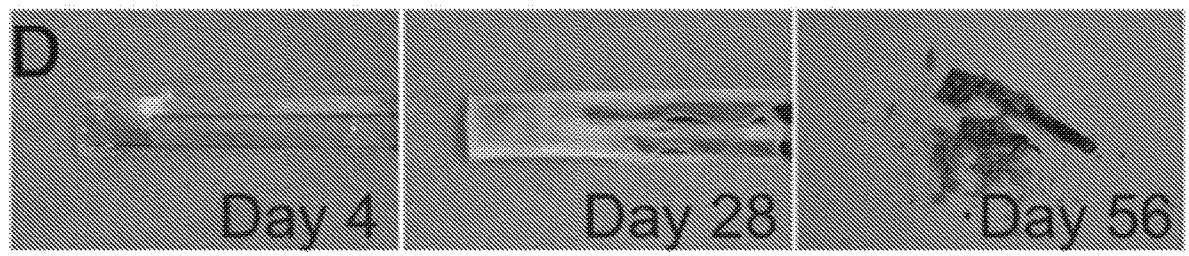
FIG. 5B illustrates a piezoelectric sensor submerged in an aqueous environment of saline solution PBS after 4 days.
FIG. 5C illustrates a piezoelectric sensor submerged in an aqueous environment of saline solution PBS after 28 days.
FIG. 5D illustrates a piezoelectric sensor submerged in an aqueous environment of saline solution PBS after 56 days.

The 4-day period was relevant to the use of this biodegradable sensor in the monitoring of important physiological pressures such as intracranial pressures in patients with acute traumatic brain injuries. Eventually, the sensor completely degraded and broke down. This can be visualized after a 56-day period in an accelerated degradation process at 74° C. (FIGS. 5B-D). Different thicknesses of the PLA encapsulators resulted in different degradation times. Therefore, longer functional lifetimes of this sensor can be obtained by engineering the thickness. Other parameters such as molecular weight can also be used to engineer degradation of the PLA encapsulating layer. This lifetime can be predefined in vitro before the implantation process. Surface-erodible biodegradable polymers such as polyorthoester, polyanhydride, polyglycerol sebacate, etc. can be used instead of PLA to precisely control and engineer the device's functional lifetime.

Figure 8:
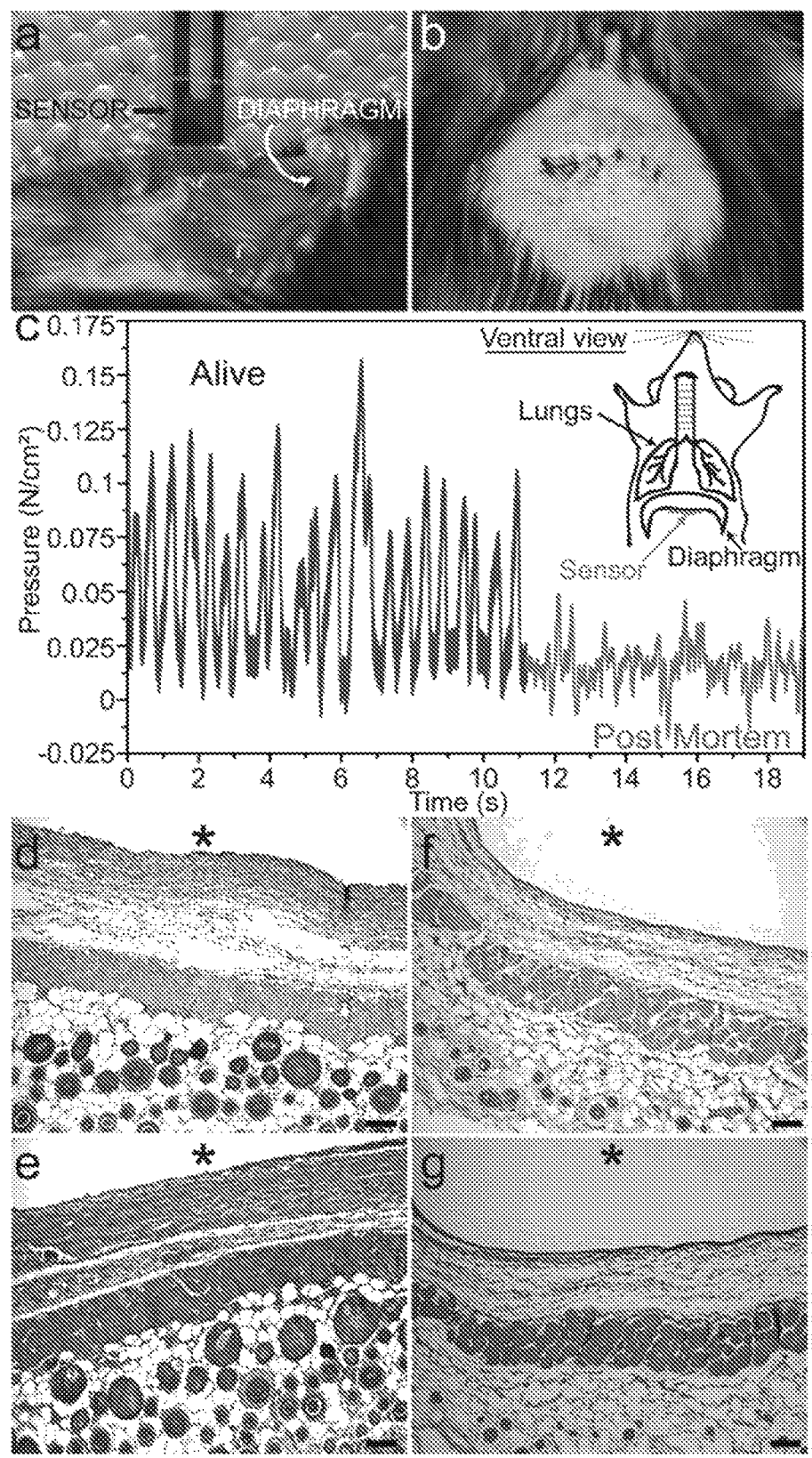
FIG. 8A illustrates in vivo force measurement and biocompatibility test. An optical image illustrates the sensor and a mouse abdominal cavity with diaphragmatic membrane.
FIG. 8B illustrates a surgical wound closed up by medical suture on abdomen of the mouse, which received an implanted PLLA sensor.
FIG. 8C illustrates data that shows the distinct force signals generated by the implanted sensor when the mouse was alive and under anesthesia (black), and when the mouse was euthanized by overdose of anesthetics (red). The inset image is a diagram describing the sensor attached to the bottom of mouse diaphragm inside the abdomen.
FIGS. 8D-G illustrate histology images of implanted PLLA sensors after 2 and 4 weeks, respectively. FIGS. D and F are histology stained by H&E while FIGS. E and G are histology stained by Masson's Trichrome. Asterisks (*) show locations of the implanted sensors. (Scale bars, 100 μm.)

As a proof of concept for the sensor's application, the device was employed to measure the pressure of diaphragmatic contraction in a mouse to detect the breathing pattern of the animal in vivo. The sensor, coated with a very thin layer of medical glue, was inserted into a small incision (8 mm) which was made below the mouse's diaphragm in the abdomen, as seen in FIG. 8A, The sensing patch alone was small (5×5 mm), allowing a complete suture of the opened wound, as seen in FIG. 8B. In the measurement, small Mo/PLA wires from the sensing patch were run through the sutured wound into an external charge amplifier circuit connected to an oscilloscope to measure electrical voltage. After letting the mouse rest for 15 min postsurgery, a clearly distinguishable signal (FIG. 8C) was observed while the anesthetized mouse was breathing under normal anesthesia, and the signal was completely suppressed after the animal was euthanized by an overdose of anesthetics. The signal generated from the mouse, when alive, has a frequency of (~2 Hz) and correlates to an input force of (~0.1 N/cm² or ~1 kPa), Both of these measurement results are consistent with previously reported respiration rates in mice. Additionally, the sensor was also able to detect abnormal breathing after anesthesia overdose until the moment the animal was deceased. This "agonal" breathing has a lower frequency and larger pressure, which is likely due to the uptake of more oxygen. The measured pressure signal was then compared to the signal generated by a non-treated PLLA sensor to verify the signal was not generated by triboelectricity and motion artifacts of the wires. These results clearly illustrate the sensor's ability to measure physiological forces and a potential use of the sensor for monitoring respiratory disorders caused by obstructive pulmonary diseases.

To verify the sensor's biocompatibility, the sensor was implanted into an area on the back of mice, which is rich with immune cells and often used for testing biocompatibility. The implants were then taken out at 2 wk and 4 wk. An histological analysis was performed by staining prepared tissue slides with hematoxylin and eosin (H&E) to observe inflammatory cells, and Masson's Trichrome blue to detect fibrosis, as depicted in FIGS. 8D-G. Immunohistochemical stains with CD64 antibody were performed to reveal macrophages. The histological images showed only a mild immune reaction without significant presence of inflammation, multinucleated giant cells, and fibrous capsules. Mild fibrosis and activated macrophages were seen at 2 wk, but remarkably reduced to normal levels at 4 wk.

Various features and advantages of the invention are set forth in the following claims.

What is claimed is:

1. A biodegradable system comprising:
   one or more magnesium wires encapsulated by poly-lactic acid;

a biodegradable piezoelectric device connected to the one or more magnesium wires, the biodegradable piezoelectric device including
a first magnesium electrode,
a second magnesium electrode, and
a polymer film positioned between the first magnesium electrode and the second magnesium electrode, the polymer film comprisinq a piezoelectric poly-L-lactic acid film,
wherein the biodegradable piezoelectric device is encapsulated by a biodegradable polymer; and
a charcie amplifier circuit connected to the biodegradable piezoelectric device, wherein the charge amplifier circuit is configured to convert a charge from the biodegradable piezoelectric device into a voltage signal and output the voltage signal to an electronic device.

2. The biodegradable system of claim 1, wherein the biodegradable piezoelectric device includes at least one selected from a group consisting of a biodegradable piezoelectric sensor, a biodegradable piezoelectric actuator, and a biodegradable piezoelectric energy harvester.

3. The biodegradable system of claim 1, wherein the biodegradable polymer polymer has a molecular weight of at least 200 kDa.

4. The biodegradable system of claim 1, wherein the biodegradable piezoelectric device has a functional lifetime proportional to at least one selected from a group consisting of an amount of piezoelectric poly-L-lactic acid film layers included in the polymer film and a molecular weight of each piezoelectric poly-L-lactic acid film layer included in the polymer film.

5. The biodegradable system of claim 4, wherein the functional life time of the biodegradable piezoelectric device increases as the amount or thickness of poly-lactic acid film layers encapsulating the sensor increases.

6. The biodegradable system of claim 4, wherein the functional life time of the biodegradable piezoelectric device increases as the molecular weight of each encapsulating poly-lactic acid film layers included in the sensor increases.

7. The biodegradable system of claim 1, wherein the polymer film includes two layers of a piezoelectric poly-L-lactic acid film.

8. The biodegradable system of claim 1, wherein the biodegradable piezoelectric device is configured to function as a sensitive multi-layer pressure transducer.

9. The biodegradable system of claim 1, wherein the biodegradable piezoelectric device is configured to output a charge in response to a pressure applied to the biodegradable piezoelectric device.

10. The biodegradable system of claim 1, wherein the biodegradable piezoelectric device has a size of approximately 0.5×0.5×0.02 cm.

11. The biodegradable system of claim 1, wherein the biodegradable piezoelectric device is configured to sense pressure within a range of approximately 1-50 mmHg.

12. A biodegradable system comprising:
one or more molybdenum wires encapsulated by poly-lactic acid;
a biodegradable piezoelectric device connected to the one or more molybdenum wires, the biodegradable piezoelectric device including
a first molybdenum electrode,
a second molybdenum electrode, and
a polymer film positioned between the first molybdenum electrode and the second molybdenum electrode, the polymer film comprising a piezoelectric poly-L-lactic acid film,
wherein the biodegradable piezoelectric device is encapsulated by a biodegradable polymer; and
a charge amplifier circuit connected to the biodegradable piezoelectric device, wherein the charge amplifier circuit is configured to convert a charge from the biodegradable piezoelectric device into a voltage signal and output the voltage signal to an electronic device.

13. The biodegradable system of claim 12, wherein the biodegradable piezoelectric device includes at least one selected from a group consisting of a biodegradable piezoelectric sensor, a biodegradable piezoelectric actuator, and a biodegradable piezoelectric energy harvester.

14. The biodegradable system of claim 12, wherein the biodegradable polymer has a molecular weight of at least 200 kDa.

15. The biodegradable system of claim 12, wherein the biodegradable piezoelectric device has a functional lifetime proportional to at least one selected from a group consisting of an amount of piezoelectric poly-L-lactic acid film layers included in the polymer film and a molecular weight of each piezoelectric poly-L-lactic acid film layer included in the polymer film.

16. The biodegradable system of claim 15, wherein the functional life time of the biodegradable piezoelectric device increases as the amount or thickness of poly-lactic acid film layers encapsulating the sensor increases.

17. The biodegradable system of claim 15, wherein the functional life time of the biodegradable piezoelectric device increases as the molecular weight of each encapsulating poly-lactic acid film layers included in the sensor increases.

18. The biodegradable system of claim 12, wherein the polymer film includes two layers of a piezoelectric poly-L-lactic acid film.

19. The biodegradable system of claim 12, wherein the biodegradable piezoelectric device is configured to function as a sensitive multi-layer pressure transducer.

20. The biodegradable system of claim 12, wherein the biodegradable piezoelectric device is configured to output a charge in response to a pressure applied to the biodegradable piezoelectric device.

21. The biodegradable system of claim 12, wherein the biodegradable piezoelectric device has a size of approximately 0.5×0.5×0.02 cm.

22. The biodegradable system of claim 12, wherein the biodegradable piezoelectric device is configured to sense pressure within a range of approximately 1-50 mmHg.

* * * * *